(12) United States Patent
Jørgensen et al.

(10) Patent No.: US 7,166,297 B2
(45) Date of Patent: Jan. 23, 2007

(54) LIPID-BASED DRUG DELIVERY SYSTEMS AGAINST PARASITIC INFECTIONS

(75) Inventors: Kent Jørgensen, Bagsværd (DK); Jesper Davidsen, Copenhagen (DK); Charlotte Vermehren, Ringsted (DK); Sven Frøkjer, Holte (DK); Ole G. Mouritsen, Odorse (DK)

(73) Assignee: LiPlasome Pharma A/S, Lyngby (DK)

( * ) Notice: Subject to any disclaimer, the term of this patent is extended or adjusted under 35 U.S.C. 154(b) by 730 days.

(21) Appl. No.: 10/239,527

(22) PCT Filed: Apr. 11, 2001

(86) PCT No.: PCT/DK01/00268

§ 371 (c)(1),
(2), (4) Date: Jan. 21, 2003

(87) PCT Pub. No.: WO01/76556

PCT Pub. Date: Oct. 18, 2001

(65) Prior Publication Data

US 2003/0162748 A1    Aug. 28, 2003

(30) Foreign Application Priority Data

Apr. 12, 2000   (DK) ............................... 2000 00616

(51) Int. Cl.
*A61K 9/127*   (2006.01)
*A61K 51/00*   (2006.01)
*A61B 5/055*   (2006.01)
*A61B 8/00*   (2006.01)

(52) U.S. Cl. ................ 424/450; 424/1.21; 424/9.321; 424/9.51

(58) Field of Classification Search ..................... None
See application file for complete search history.

(56) References Cited

U.S. PATENT DOCUMENTS 5,827,836 A    10/1998    Peterson et al.
6,835,718 B2 *  12/2004    Kosak ........................ 514/58

FOREIGN PATENT DOCUMENTS

DE    4408011         11/1995
EP      370491 A2  *  5/1990
JP    EP 03070491      5/1990

OTHER PUBLICATIONS

Hart, D. et al., Chemical Abstracts, vol. 130, No. 25, Jun. 21, 1999.
Xia, J. et al., Tetrahedron: Asymmetrie, vol. 8, No. 18, Sep. 25, 1997, pp. 3131-3142.

* cited by examiner

*Primary Examiner*—S. Tran
(74) *Attorney, Agent, or Firm*—Birch, Stewart, Kolasch & Birch, LLP

(57) ABSTRACT

The present invention is directed to a lipid-based delivery system for administration of an active drug substance selected from lysolipid derivatives which are particularly useful in the treatment or detection of parasitic infections, especially parasitic infections which cause an elevated $PLA_2$ level in the infected mammal. Preferred parasitic infections are infections wherein the life cycle of the parasite involves the liver and/or spleen of the infected organism.

12 Claims, 17 Drawing Sheets

Fig. 1
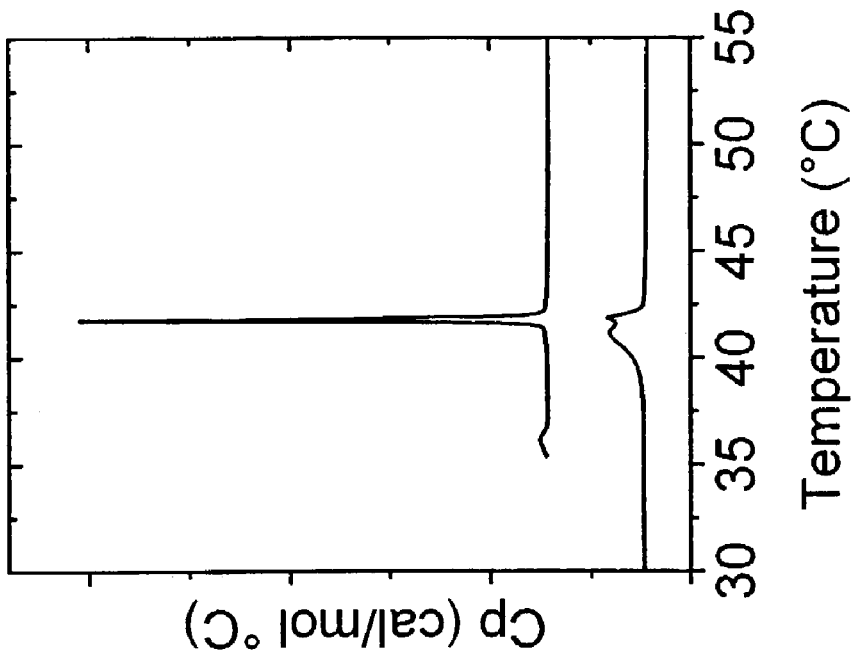
a)
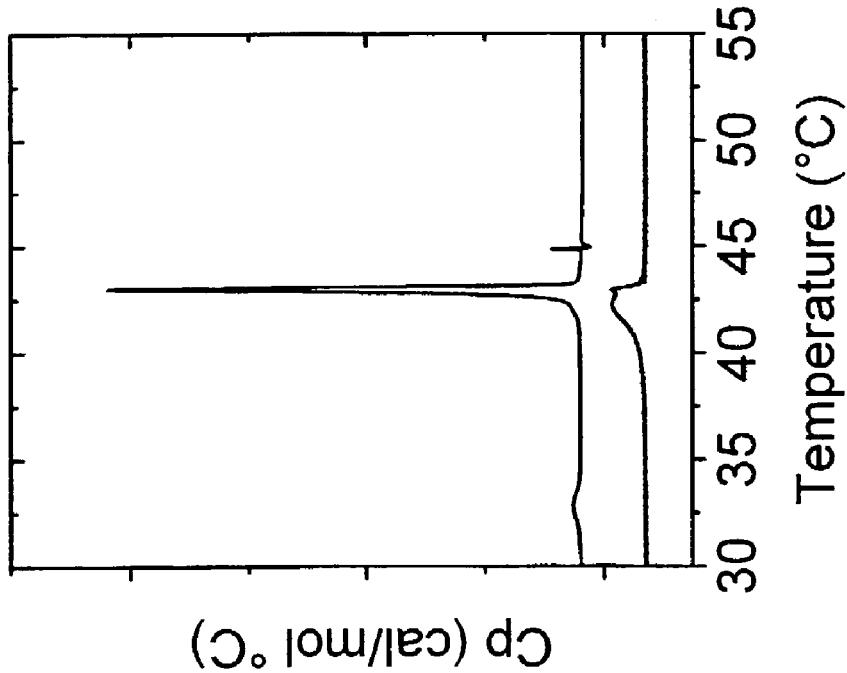
b)

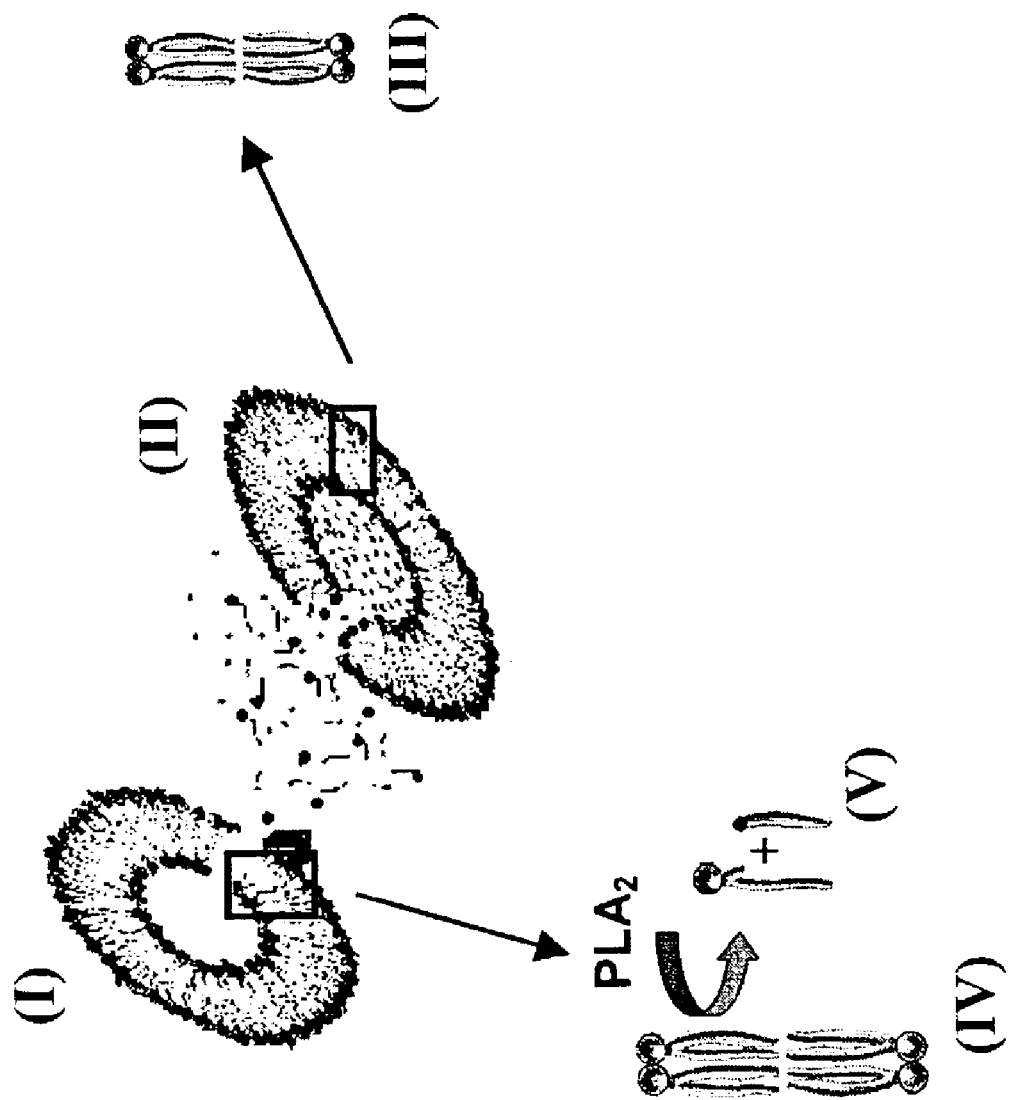

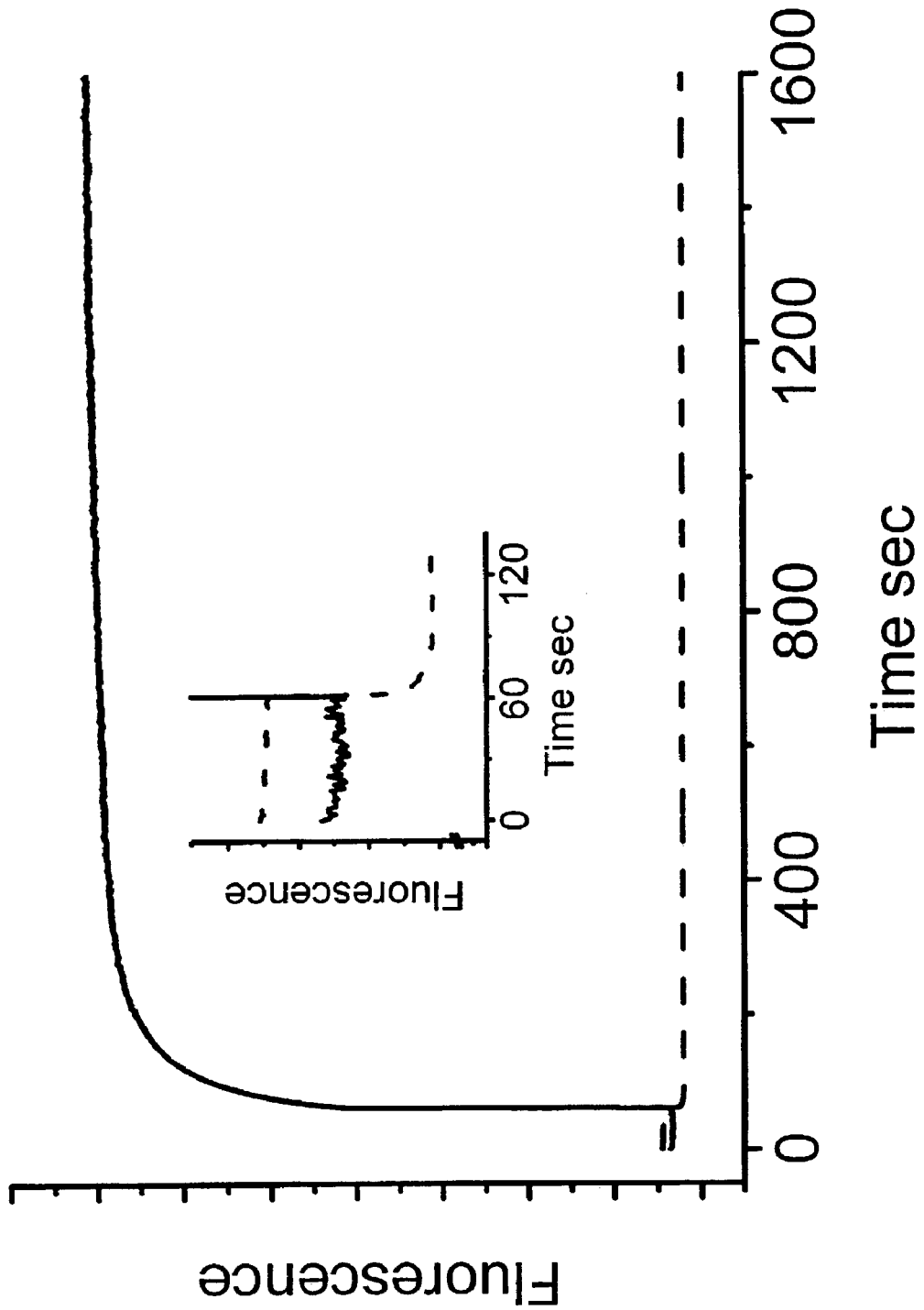

LIPID-BASED DRUG DELIVERY SYSTEMS AGAINST PARASITIC INFECTIONS

This application is the national phase under 35 U.S.C. § 371 of PCT International Application No. PCT/DK01/00268 which has an International filing date of Apr. 11, 2001.

FIELD OF THE INVENTION

The invention relates to lipid-based pharmaceutical compositions for use in the treatment or detection of parasitic infections.

BACKGROUND OF THE INVENTION

U.S. Pat. No. 5,827,836 discloses retinoyl substituted glycerophophoethanolamines. It is stated that the compounds and salts thereof exhibit antitumor, anti-psoriatic and anti-inflammatory activities. A possible class of compounds has a fatty ether substituent in the 1-position, a retinoid ester (retinoyl) substituent in the 2-position and a phosphoethanolamine substituent in the 3-position. It is mentioned that some of the compounds can be presented in a liposome formulation.

U.S. Pat. No. 4,372,949 discloses a carcinostatic and immunostimulating agent containing a lysophospholipid and a phospholipid. Examples of compounds are 3-phosphorylcholine having a $C_{5-22}$-acyloxy or $C_{5-22}$-alkoxy substituent in the 1-position, and a hydrogen, hydroxy, $C_{1-5}$-acyloxy or $C_{1-5}$-alkoxy substituent in the 2-position. It is mentioned that the agents can be dispersed in the form of micelles or lipid vesicles.

U.S. Pat. No. 5,484,911 discloses nucleoside 5'-diphosphate conjugates of ether lipids which exhibit antiviral activity. The compounds may have a fatty ether/thioether substituent in the sn-1-position and a fatty acid ester substituent in the sn-2-position. The compounds are designed so as to penetrate the cell membrane whereafter the nucleoside drug is liberated by cleavage by intracellular phosphatases. It is furthermore suggested that the also liberated ether lipids may be subsequently cleaved by intracelluar phospholipase $A_2$. It is suggested that the conjugates can be presented in the form of micelles which more easily can be taken up by macrophages.

U.S. Pat. No. 4,622,392 discloses cytotoxic compounds of the nucleotide-lipid conjugate type.

ES 2 034 884 discloses 2-aza-phospholipider as $PLA_2$ inhibitors. Similarly, de Haas et al (Biochem. Biophys. Acta, Lipid and Lipids Metabolism, 1167 (1993) No. 3, pp 281–288, discloses inhibition of pancreatic $PLA_2$ by (R)-2-acylamino phospholipid analogues.

Hoffman et al., Blood, Vol. 63, No. 3 (March), 1984, pp 545–552, discloses the cytotoxicity of PAF and related alkyl-phospholipid analogues in human Leukemia cells.

WO 94/09014 discloses phosphoric acid esters as $PLA_2$ inhibitors. A group of the inhibitors are 1-O-phospho-2-O—($C_{2-21}$-acyl)-($C_{12-24}$-alkanes).

Xia and Hui discloses the chemical synthesis of a series of ether phospholipids from D-mannitol and their properties as tumor-cytotoxic agents.

U.S. Pat. No. 5,985,854, U.S. Pat. No. 6,077,837, U.S. Pat. No. 6,136,796 and U.S. Pat. No. 6,166,089 describe prodrugs with enhanced penetration into cells, which are particular useful for treating a condition or disease in a human related to supranormal intracellular enzyme activity.

The prodrugs may be sn-2-esters of lysophospholipids. Such drugs are designed so as to be cleaved by intracelluar phospholipase $A_2$.

Vadas et al. (Infection and Immunity, 60 (1992) 3928–3931 and Am. J. Trop. Hyg. 49 (1993) 455–459) describe the induction of circulating $PLA_2$ expression in humans with malaria infections caused by *Plasmodium falciparum*.

Lux et al. (Biochem. Parasitology 111 (2000) 1–14) describe the anti-leishmania action of certain ether-lipid analogues which is believed to be caused by the interference with important biosyntheses of the parasite.

BRIEF DESCRIPTION OF THE INVENTION

The present invention is directed to drug delivery systems which are particularly useful in the treatment of parasitic infections especially parasitic infections wherein the life cycle of the parasite involves the liver and/or spleen of the infected organism. The liposomes of the present invention are only degraded to a very low extend by enzymes present in the blood stream, whereas said liposomes are up-concentrated and degraded in the liver and/or spleen by the macrophages present in these organs. This degradation of the liposomes releases constituents which are designed to be toxic for various types of parasites. In one embodiment of the present invention the lysolipids released from the liposome are toxic to the parasites, in another embodiment anti-parasitic drugs are encapsulated in the liposomes. In a further embodiment a combination of liposomes made from lipids which are toxic to parasites in which anti-parasitic drugs are encapsulated. Accordingly, a highly efficient and indirectly specific release of substances toxic to parasites is achieved in the case of parasitic infection of tissues characterised by the presence of macrophages, such as the liver and/or the spleen.

Yet another embodiment of the present invention is the diagnostic use of the presently described drug delivery systems, wherein the drug delivery system carries a label which, by the action described above, is specifically directed towards the tissue or organs being infected by the parasite.

DESCRIPTION OF THE DRAWINGS

FIG. 1 Heat capacity curves obtained using differential scanning calorimetry. (a) Multilamellar, MLV (the upper curve) and unilamellar, LUV (the bottom curve) liposomes made of 1 mM 1-O-hexadecyl-2-hexadecanoyl-sn-glycero-3-phosphocholine (1-O-DPPC). (b) MLV (the upper curve) and LUV (the bottom curve) liposomes made of dipalmitoylphosphatidylcholine (DPPC).

FIG. 11 Schematic illustration of a liposomal drug-targeting principle involving accumulation of the liposomal drug carriers the RES in porous diseased tissue and subsequent release of drug and transport across the target membrane via extracellular PLA$_2$ activity.
(I) Prodrug carrier liposome
(II) Non-degradable target liposomal membrane
(III) Non-hydrolysable ether-lipids
(IV) Proenhancer (lipid), prodrug (i.e. monoether-lipid), proactivator (lipid)
(V) Enhancers (lysolipid+fatty acid), drugs (i.e. ether-lysolipid and fatty acid derivatives), PLA$_2$ activators (lysolipid+fatty acid)

FIG. 16. Characteristic reaction time profile at 41° C. for rat phospholipase catalysed hydrolysis of negatively charged liposomes. The catalytic reaction was initiated by adding cell-free peritoneal fluid to 2.5 ml of the thermostated liposome suspension equilibrated for 60 sec prior to addition of peritoneal fluid. The hydrolysis reaction is monitored by monomer fluorescence (solid line) and eximer fluorescence (dashed line) from bis-py-DPC. After adding undiluted peritoneal fluid, at 60 sec, to the equilibrated liposome suspension a sudden increase in monomer fluorescence, and a simultaneously decrease in eximer fluorescence is observed as the bis-py-DPC substrate is hydrolysed. The insert shows the reaction time profile of the first 120 sec.

DETAILED DESCRIPTION OF THE INVENTION

Figure 2:
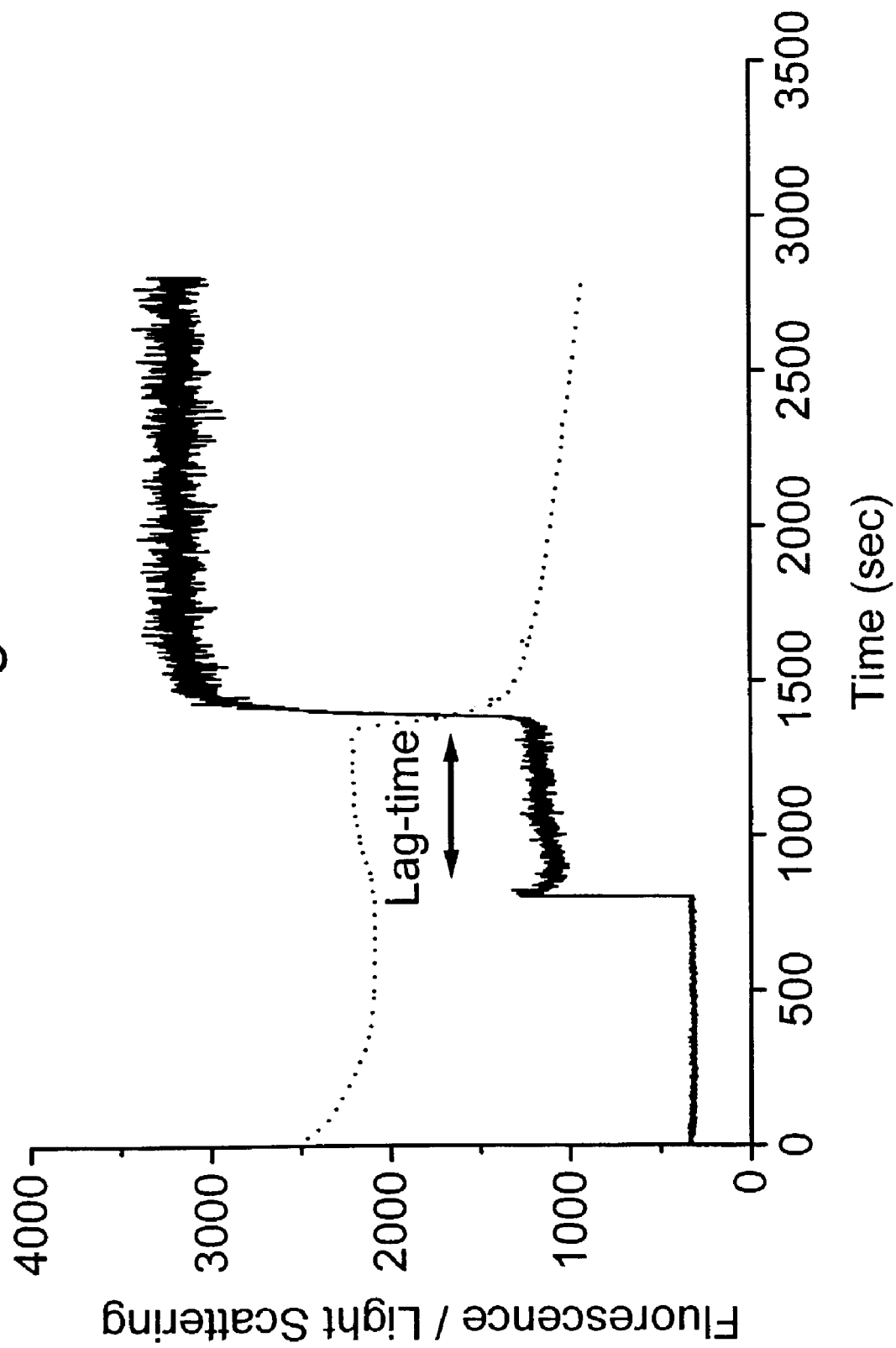
FIG. 2. Characteristic reaction time profile at 41° C. for phospholipase $A_2$, $PLA_2$, (A. piscivorus piscivorus) hydrolysis of unilamellar liposomes composed of 1-O-DPPC. The $PLA_2$ hydrolysis reaction is monitored by intrinsic fluorescence (solid line) from the enzyme and 90° static light scattering (dashed lines) from the lipid suspension. After adding $PLA_2$, at 800 sec to the equilibrated liposome suspension a characteristic lag-time follows before a sudden increase in the catalytic activity takes place. Samples for HPLC were taken before adding the enzyme and 20 minutes after the observed lag time.

One of the important features of the present invention is the realisation of the rapid uptake of liposomes in vivo by cells of the mononuclear phagocytic system (MPS). The MPS comprises the macrophages, one of the most important components of the immune system especially in clearance of foreign particles, including liposomes. The macrophages resides in various organs and tissues, e.g. in connective tissue (as histiocytes), in the liver (Kupffer cells) and as free and fixed macrophages in the spleen, bone marrow and lymph nodes.

When liposomes in general are administered intravenously they are typically removed from the circulation by the macrophages of the liver, spleen and bone marrow. This removal consists of a first opsonization by blood proteins followed by macrophage uptake of these marked liposomes. The immune opsonins are comprised by immunoglobulins and complement proteins, and although each opsonin has its own interaction and confers different fates, it seems that liver sequestration is complement mediated and the spleen removes the opsonized liposomes in general. The enhanced clearance of the liposomes of the present invention obtained by the opsonization can be characterised as passive targeting.

As the MPS uptake of liposomes results in the accumulation of the liposomes in tissues like the liver, the spleen and the bone marrow it enables a targeting directed against parasitic infections of these tissues. The liposomes of the present invention comprises constituents which can act as a label for detecting parasite infected tissue/organs or can act as anti-parasitic drugs when released from the liposomes to the tissues of a mammal suffering from a parasitic infection.

One embodiment of the present invention is thus a method for the treatment of parasitic infections which is characterised by an increased level of $PLA_2$ in a mammal, preferably a human, by administering to the mammal an efficient amount of a lipid-based delivery system for administration of an active drug substance selected from lysolipid derivatives, wherein the active drug substance is present in the lipid-based system in the form of a prodrug, said prodrug being a lipid derivative having (a) an aliphatic group of a length of at least 7 carbon atoms and an organic radical having at least 7 carbon atoms, and (b) a hydrophilic moiety, said prodrug furthermore being a substrate for extracellular phospholipase A2 to the extent that the organic radical can be hydrolytically cleaved off, whereas the aliphatic group remains substantially unaffected, whereby the active drug substance is liberated in the form of a lysolipid derivative which is not a substrate for lysophospholipase.

A further embodiment is a method for the treatment of parasitic infections which is characterised by an increased level of $PLA_2$ in a mammal, preferably a human, by administering to the mammal an efficient amount of the lipid based delivery system described above for administration of an second substance, wherein the second substance is a anti-parasitic drug incorporated in said system.

In one specific embodiment of the present invention the increased level of $PLA_2$ is localized to a specific tissue and/or organ of the mammal, said tissue and/or organ being infected by the parasite. Especially a situation wherein the parasitic infection involves the liver and/or the spleen and/or the bone marrow of the mammal is comprised by the present invention.

The treatment is preferably performed by systemically administration of the lipid based delivery system of the present invention, even more preferably administered parenterally by injection such as intravenous injection.

Yet another embodiment of the present invention is a method for diagnosing a parasitic infection which is characterised by an increased level of $PLA_2$ of the infected tissue by administering to the mammal an efficient amount of the lipid based delivery system described above for administration of an second substance, wherein the second substance is a label incorporated in said system. By administering such a construct to a patient suspected of having a parasitic infection it is possible to determine if the patient is infected and in the case of a parasitic infection the localized areas of the patients body harbouring the parasite is identified. The localized deliverance of the diagnostic agent—the label—enables the use of diagnostic imaging tools such as positron emission tomography (PET), X-ray, gamma-scintigraphy, magnetic resonance (MR) imaging, computed tomography (CT) imaging and ultrasonography.

The labels applicable for the medical imaging are selected from the group consisting of diagnostic radionuclides, such as $^{111}$In, $^{99m}$Tc, $^{67}$Ga, $^{11}$C; paramagnetic ions, such as Gd and Mn, and iron oxide; gas, such as air, argon, nitrogen; Iodine; bromine and barium.

Target Parasitic Organisms

The liposomes of the present invention are able to deliver various ether-lipid analogues to tissues harbouring parasites due to increased levels of $PLA_2$ levels of said tissue. The ether-lipid analogues have been shown to result in perturbation of key enzymes involved in e.g. alkyl-phospholipid biosynthesis of parasites such as Leishmania and Trypanosomas (Lux et al. Biochem. Parasitology 111 (2000) 1–14) and are therefore toxic to the parasites if administered in sufficient amount.

As the liver, spleen and bone marrow are organs/tissues wherein high concentrations of macrophages can be found, targeting parasites inhabiting these organs is preferred because of resulting accumulation of liposomes of the present invention, but other tissues characterized by having increased $PLA_2$ levels during parasitic infection may also be of interest.

Furthermore, parasitic infections which are characterised by highly elevated levels of circulating $PLA_2$, such as malaria-causing parasites, e.g. caused by *Plasmodium falciparum*, are also targets for treatment with liposomes of the present invention. This characteristic of elevated levels of circulating $PLA_2$ of malaria infections caused by the parasite *Plasmodium falciparum* has been described by e.g. Vadas et al. (Infection and Immunity, 60 (1992) 3928–3931 and Am. J. Trop. Hyg. 49 (1993) 455–459).

Examples of parasite infections resulting in increased $PLA_2$ level of the parasite harbouring tissue are given below.

*Leishmania*

Members of the genus *Leishmania* has the potential to infect various vertebrate species, including humans, dogs, and rodents and the various types of leishmaniasis are confined primarily, but not exclusively, to Central and South America, central Africa, and parts of southern and central Asia.

The life cycle of members of the genus involve a vertebrate host e.g. the human and a vector that transmits the parasite between vertebrate hosts. In the case of *Leishmania* the vector is various species of *Phlebotomus* sand flies.

The characteristic morphological form taken by the *Leishmania* paracite in the vector is the promastigote, and in this stage it reproduces asexually in the vector's gut. Upon biting the vertebrate host, promastigotes from the vector are injected into the vertebrate host. After the entrance into the vertebrate host he promastigotes change into a form called amastigote. The amastigote reproduces in the host's cells, and when the vertebrate host cell eventually dies, the amastigotes are released and will potentially infect other cells. The symptoms and pathology associated with leishmaniasis result from the amastigotes killing the host's cells.

*Leishmania* is the cause of several different conditions depending on the site of infection of the vertebrate host. In some diseases the amastigotes do not spread beyond the site of the vector's bite which then results in a "cutaneous leishmaniasis" also known as oriental sore, Jericho boil, Aleppo boil, or Dehli boil. These conditions often heal spontaneously. In other instances the amastigotes may spread to the visceral organs, i.e. the liver and the spleen, which results in "visceral leishmaniasis" also known as kala-azar or Dum-Dum fever. Furthermore, the amastigotes may spread to the mucous membranes of the mouth and nose, resulting in the condition of "mucocutaneous leishmaniasis" also known as espundia or uta. Left untreated, these latter diseases result in high rates of mortality.

Non-limiting examples of *Leishmania* species are *Leishmania major* Friedlin, *Leishmania* (viannia) gr., *Leishmania mexicana, Leishmania tropical Leishmania donovani* (infantum), *Leishmania aethiopica, Leishmania amazonensis, Leishmania enrieltii, Leishmania chagasi* and *Leishmania pifanoi*.

Traditional anti-leishmanial therapy agents are compounds like the pentavalent antimony compounds sodium stibogluconate (Pentosram™) and meglumine antimonate (Glucantime™), other drugs are amphotericin, metronidazole, allopurinol and pentamidine, furthermore paromomycin and interferon gamma.

Both for malaria treatment and *Leishmania* treatment a new drug, Licochocone A, which was originally isolated from the roots of Chinese licorice, has been proposed.

*Trypanosoma*

Three main species of trypanosomes causes disease in humans, these are *Trypanosoma gambiense* and *Trypanosoma rhodesiense*, which both cause sleeping sickness in Africa, and *Trypanosoma cruzi*, which causes Chargas' disease in South America.

Both types of disease are characterised by bouts of parasitaemia and fever. The damage to the organs is caused toxins released by the parasites.

The most common vector for transmitting the trypanosomes causing sleeping sickness is the tsetse fly Glossina sp. The species that cause human African trypanosomiasis (sleeping sickness) also infect wild animals and can be transmitted from these animals to humans (zoonotic infections).

In humans, *Trypanosoma cruzi* is found as both an intracellular form, the amastigote, and as a trypomastigote form in the blood. The vector for Chagas' disease is a "true bug" (Hemiptera) such a *Triatoma, Rhodnius,* or *Panstongylus* which ingests amastigotes or trypomastigotes when it feeds. In the vector the parasite reproduces asexually and metacyclic trypomastigotes are found in the vector's hindgut. The vector defecates on the host's skin at the same time that it feeds, and the metacyclic trypomastigotes enter the host's body, most often by being "rubbed in" to the vector's bite or the mucous membranes of the eye, nose, or mouth. In the human host, Chagas' disease affects primarily the nervous system and heart but also sometimes the liver, spleen, bone and intestine. Chronic infections result in various neurological disorders, including dementia, megacolon, and megaesophagus, and damage to the heart muscle. Left untreated, Chagas' disease is often fatal.

The main traditional drugs used for treatment of sleeping sickness are suramin and pentamidine. Traditional drugs for Chargas' disease are primaquine, puromycin and nitrofurantoin derivatives, but none of these drugs have proven really effective in the treatment for this condition.

Non-limiting examples of *Trypanosoma* species are *Trypanosoma cruzi* (causing Chargas' disease), *Trypanosoma brucei, Trypanosoma equiperdum* and *Trypanosoma evansi*.

*Plasmodium-malaria*

Malaria is one of the major killer diseases of the world causing an estimated one—two million deaths annually. Malaria is caused by various species of plasmodia. The female anopheline mosquito injects sporozoites, which in the liver can develop into merozoites. The merozoites infect red blood cells and in the red blood cells the merozoites grow and eventually cause the cell to rupture and release more merozoites most of which infect other red blood cells and repeat the cycle. Some of the merozoites evolve into gametocytes, which infect the female anopheline mosquito.

The rupture of the blood cells and the release of merozoites cause the fever associated with malaria. The frequency of the fever attacks depends on the species of *Plasmodium. Plasmodium falciparum, Plasmodium vivax* and *Plasmodium ovale* causes red blood cell rupture after 48 hrs. and the malaria patient therefor experiences violent fever attacks every third day. *Plasmodium malariae* causes red blood cell rupture every 72 hrs.

*Entamoeba histolytica*

This protozoan parasite infects the lower bowel and frequently causes amebic dysentery. If untreated can lead to death. This amoebae is not restricted to the large intestine but can spread to other soft organs, particularly the liver, where it can produce large abscesses over the course of a few years. People become infected by ingesting the amebic cyst in contaminated food or water.

The Oriental Liver Fluke:

The life cycle of the oriental liver fluke Chlornorchis sinensis starts with a miracidium infecting a snail. In the snail the miracidium develops into a cercariae. The cercariae leaves the snail and penetrate the skin of a fish. In the fish the cercariae encrysts itself in the mussel tissue and when the fish raw or undercooked fish is eaten the immature worm is released and it migrates to the liver where it matures causing damage to the liver.

Lipid Derivatives

The lipid-based delivery systems (liposomes or micelles) relies on lipid derivatives having (a) an aliphatic group of a length of at least 7 carbon atoms and an organic radical having at least 7 carbon atoms, and (b) a hydrophilic moiety, said prodrug furthermore being a substrate for extracellular phospholipase A2 to the extent that the organic radical can be hydrolytically cleaved off, whereas the aliphatic group remains substantially unaffected, whereby the active drug substance is liberated in the form of a lysolipid derivative which is not a substrate for lysophospholipase.

Although the terms "lipid" and "lysolipid" (in the context of phospholipids) will be well-known terms for the person skilled in the art, it should be emphasised that, within the present description and claims, the term "lipid" is intended to mean triesters of glycerol of the following formula:

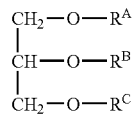

wherein $R^A$ and $R^B$ are fatty acid moieties ($C_{9-30}$-alkyl/alkylene/alkyldiene/alkyltriene/-alkyltetraene-C(=O)—) and $R^C$ is a phosphatidic acid ($PO_2$—OH) or a derivative of phosphatidic acid. Thus, the groups $R^A$ and $R^B$ are linked to the glycerol backbone via ester bonds.

The term "lysolipid" is intended to mean a lipid where the $R^B$ fatty acid group is absent (e.g. hydrolytically cleaved off), i.e. a glycerol derivative of the formula above where $R^B$ is hydrogen, but where the other substituents are substantially unaffected. Conversion of a lipid to a lysolipid can take place under the action of an enzyme, specifically under the action of cellular as well as extracellular $PLA_2$.

The terms "lipid derivative" and "lysolipid derivative" are intended to cover possible derivatives of the above possible compounds within the groups "lipid" and "lysolipid", respectively. Examples of biologically active lipid derivatives and iysolipid derivatives are given in Houlihan, et al., Med. Res. Rev., 15, 3, 157–223. Thus, as will be evident, the extension "derivative" should be understood in the broadest sense.

Within the present application, lipid derivatives and lysolipids should however fulfill certain functional criteria (see above) and/or structural requirements. It is particularly relevant to note that the suitable lipid derivatives are those which have (a) an aliphatic group of a length of at least 7, preferably at least 9, carbon atoms and an organic radical having at least 7 carbon atoms, and (b) a hydrophilic moiety. It will be evident that the aliphatic group and the organic radical will correspond to the two fatty acid moieties in a normal lipid and that the hydrophilic moiety will correspond to the phosphate part of a (phospho)lipid or a bioisoster thereof.

Thus, one element of the idea behind the present invention is to exploit the increased level of extracellular $PLA_2$ activity in localised areas of the body of a mammal, in particular areas of parasitic infection, the lipid derivatives which can be utilised within the present invention should be substrates for extracellular $PLA_2$, i.e. the lipid derivatives should be able to undergo hydrolytic, enzymatic cleavage of the organic radical corresponding to the fatty acid in the 2-position in a lipid. Extracellular $PLA_2$ is known to belong to the enzyme class (EC) 3.1.1.4. Thus by reference to (extracellular) $PLA_2$ should be understood all extracellular enzymes of this class, e.g. lipases, which can induce hydrolytic cleavage of the organic radical corresponding to the fatty acid in the 2-position in a lipid. One particular advantage of the lipid-based delivery system (as liposomes and micelles) is that extracellular $PLA_2$ activity is significantly increased towards organised substrates as compared to monomeric substrates.

In view of the requirement to hydrolysability by extracellular $PLA_2$, it is clear that the organic radical (e.g. aliphatic group) is preferably linked via an ester functionality which can be cleaved by extracellular $PLA_2$, preferably so that the group which is cleaved off is a carboxylic acid.

Furthermore, an important feature is that the aliphatic group (the group corresponding to the fatty acid in the 1-position in a lipid) of the lipid derivative, i.e. the lysolipid derivative after cleavage by extracellular $PLA_2$, is substantially unaffected by the action of extracellular $PLA_2$. By "substantially unaffected" is meant that the integrity of the aliphatic group is preserved and that less than 1 mol %, preferably less than 0.1 mol %, of the aliphatic group (the aliphatic group in the 1-position) is cleaved under the action of extracellular $PLA_2$.

Also, the lysolipid derivative resulting from the hydrolytic cleavage of the organic radical should not in itself be a substrate for lysophospholipase. Lysophospholipase is known to belong to the enzyme class (EC) 3.1.1.5. Thus by reference to lysophospholipase should be understood all enzymes of this class that catalyses the reaction lyso(phospho)lipid+water yielding phosphoglycerol+fatty acid. The term "not a substrate for lysophospholipase" is intended to mean that lysophospholipase has an activity of less than 1% towards the substrate compared with the corresponding esterlipid, i.e. virtually not enzymatic activity.

Suitable examples of such lysolipid derivatives are those which will not undergo hydrolytical cleavage under the action of lysophospholipases. Thus, the lysolipid derivatives are in particular not lysolipids and lysolipid derivatives which have an ester linkage in the 1-position of the lysolipid or the position of a lysolipid derivative which corresponding to the 1-position of a lysolipid.

One preferred class of lipid derivatives for incorporation in the lipid-based delivery systems can be represented by the following formula:

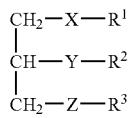

wherein

X and Z independently are selected from O, $CH_2$, NH, NMe, S, S(O), and $S(O)_2$, preferably from O, NH, NMe and $CH_2$, in particular O;

Y is —OC(O)—, Y then being connected to $R^2$ via either the oxygen or carbonyl carbon atom, preferably via the carbonyl carbon atom;

$R^1$ is an aliphatic group of the formula $Y^1Y^2$;

$R^2$ is an organic radical having at least 7 carbon atoms, such as an aliphatic group having a length of at least 7, preferably at least 9, carbon atoms, preferably a group of the formula $Y^1Y^2$;

where $Y^1$ is —$(CH_2)_{n1}$—$(CH=CH)_{n2}$—$(CH_2)_{n3}$—$(CH=CH)_{n4}$—$(CH_2)_{n5}$—$(CH=CH)_{n6}$—$(CH_2)_{n7}$—$(CH=CH)_{n8}$—$(CH_2)_{n9}$, and the sum of n1+2n2+n3+2n4+n5+2n6+n7+2n8+n9 is an integer of from 9 to 29; n1 is zero or an integer of from 1 to 29, n3 is zero or an integer of from 1 to 20, n5 is zero or an integer of from 1 to 17, n7 is zero or an integer of from 1 to 14, and n9 is zero or an integer of from 1 to 11; and each of n2, n4, n6 and n8 is independently zero or 1; and $Y^2$ is $CH_3$ or $CO_2H$; where each $Y^1$–$Y^2$ independently may be substituted with halogen or $C_{1-4}$-alkyl, but preferably $Y^1$–$Y^2$ is unsubstituted, $R^3$ is selected from phosphatidic acid ($PO_2$—OH), derivatives of phosphatidic acid and bioisosters to phosphatic acid and derivatives thereof.

As mentioned above, preferred embodiments imply that Y is —OC(O)— where Y is connected to $R^2$ via the carboxyl atom. The most preferred embodiments imply that X and Z are O and that Y is —OC(O)— where Y is connected to $R^2$ via the carboxyl atom. This means that the lipid derivative is a 1-monoether-2-monoester-phospholipid type compound.

Another preferred group of lipid derivatives is the one where the group X is S.

In one embodiment, $R^1$ and $R^2$ are aliphatic groups of the formula $Y^1$ $Y^2$ where $Y^2$ is $CH_3$ or $CO_2H$, but preferably $CH_3$, and where $Y^1$ is —$(CH_2)_{n1}(CH=CH)_{n2}(CH_2)_{n3}(CH=CH)_{n4}$—$(CH_2)_{n5}(CH=CH)_{n6}(CH_2)_{n7}(CH=CH)_{n8}(CH_2)_{n9}$; the sum of n1+2n2+n3+2n4+n5+2n6+n7+2n8+n9 is an integer of from 9 to 23; that is, the aliphatic group, $Y^1Y^2$, is from 10–24 carbon atoms in length. n1 is equal to zero or is an integer of from 1 to 23; n3 is equal to zero or is an integer of from 1 to 20; n5 is equal to zero or is an integer of from 1 to 17; n7 is equal to zero or is an integer of from 1 to 14; n9 is equal to zero or is an integer of from 1 to 11; and each of n2, n4, n6 and 8 is independently equal to zero or 1.

In one embodiment, one or more of the aliphatic groups $R^1/R^2$ or the $R^3$ groups include a label, e.g. halogens (bromo, iodo) or barium atoms which are particular suitable for computed tomography (CT) imaging, or are enriched with unstable isotopes, e.g. $^{11}C$ which is particularly useful for PET scanning purposes.

Although the aliphatic groups may be unsaturated and even substituted with halogens (flouro, chloro, bromo, iodo) and $C_{1-4}$-groups (i.e. yielding branched aliphatic groups), the aliphatic groups as $R^1$ and $R^2$ are in one embodiment preferably saturated as well as unbranched, that is, they preferably have no double bonds between adjacent carbon atoms, each of n2, n4, n6 and n8 then being equal to zero. Accordingly, $Y^1$ is preferably $(CH_2)_{n1}$. More preferably (in this embodiment), $R^1$ and $R^2$ are each independently $(CH_2)_{n1}CH_3$, and most preferably, $(CH_2)_{17}CH_3$ or $(CH_2)_{15}CH_3$. In alternative embodiments, the groups can have one or more double bonds, that is, they can be unsaturated, and one or more of n2, n4, n6 and n8 can be equal to 1. For example, when the unsaturated hydrocarbon has one double bond, n2 is equal to 1, n4, n6 and n8 are each equal to zero and $Y^1$ is $(CH_2)_{n1}$ CH=CH$(CH_2)_{n3}$. n1 is equal to zero or is an integer of from 1 to 21, and n3 is also zero or is an integer of from 1 to 20, at least one of n1 or n3 not being equal to zero.

In one particular embodiment, the lipid derivatives are those which are monoether lipids where X and Z are O, $R^1$ and $R^2$ are independently selected from alkyl groups, $(CH_2)_n CH_3$, where n is 11, 12, 13, 14, 15, 16, 17, 18, 19, 20, 21, 22, 23, 24, 25, 26, 27, 28, or 29, preferably 14, 15 or 16, in particular 14; Y is —OC(O)—, Y then being connected to $R^2$ via the carbonyl carbon atom.

With respect to the hydrophilic moiety (often known as the "head group") which corresponds to $R^3$, it is believed that a wide variety of groups corresponding to phosphatidic acid ($PO_2$—OH), derivatives of phosphatidic acid and biososters to phosphatic acid and derivatives thereof can be used. As will be evident, the crucial requirement to $R^3$ is that the groups should allow for enzymatic cleavage of the $R^2$ group (actually $R^2$—C(=O) or $R^2$—OH) by extracellular $PLA_2$. "Bioisosters to phosphatidic acid and derivatives thereof" indeed implies that such groups—as phosphatidic acid—should allow for enzymatic cleavage by extracellular $PLA_2$.

$R^3$ is typically selected from phosphatidic acid ($PO_2$—OH), phosphatidylcholine ($PO_2$—O—$CH_2CH_2N(CH_3)_3$), phosphatidylethanolamine ($PO_2$—O—$CH_2CH_2NH_2$), N-methyl-phosphatidylethanolamine($PO_2$—O—$CH_2CH_2NCH_2$), phosphatidylserine, phosphatidylinositol, and phosphatidylglycerol ($PO_2$—O—$CH_2CHOHCH_2OH$). Other possible derivatives of phosphatidic acid are those where dicarboxylic acids, such as glutaric, sebacic, succinic and tartaric acids, are coupled to the terminal nitrogen of phosphatidylethanolamines, phosphatidylserine, phosphatidylinositol, etc.

One highly interesting aspect is the possibility of modifying the pharmaceutical effect of the lipid derivative by modifying the group $R^2$. It should be understood that $R^2$ should be an organic radical having at least 7 carbon atoms) (such as an aliphatic group having a certain length (at least 7, preferably 9, carbon atoms)), a high degree of variability is possible, e.g. $R^2$ need not necessarily to be a long chain residue, but may represent more complex structures.

Generally, it is believed that $R^2$ may either be rather inert for the environment in which it can be liberated by extracellular $PLA_2$ or that $R^2$ may play an active pharmaceutical role, typically as an auxiliary anti-parasitic drug substance, such as allopurinol, amodiaquine, amphotericin, antifolates, artemether+benflumetol combination, artemisinin, derivatives, chloroproguanil, Chloroquine, combination of atovaquone and proguanil HCL (salesname Malarone™), dapsone, Doxycycline, halofantrine, interferon gamma, Licochalcone A, Mefloquine, meglumine antimonate, metronidazole, nitrofurantoin derivatives, paromomycin, pentamidine, primaquine, primaquine, Proguanil, (Chloroquine plus proguanil), puromycin, pyrimethamine, pyronaridine, quinine and sodium stibogluconate or as an efficiency modifier for the lysolipid derivative and/or any other (second) substances present in the environment.

In one embodiment, one or more of the aliphatic groups $R^1/R^2$ or the $R^3$ groups include a label, e.g. halogens (bromo, iodo) or barium atoms which are particular suitable for computed tomography (CT) imaging, or are enriched with unstable isotopes, e.g. $^{11}C$ which is particularly useful for PET scanning purposes.

In some embodiments, the group $R^2$ will be a long chain residue, e.g. a fatty acid residue (the fatty acid will include a carbonyl from the group Y). This has been described in detail above. Interesting examples of auxiliary drug substances as $R^2$ within this subgroups are polyunsaturated acids, e.g. oleate, linoleic, linolenic, as well as derivatives of arachidonoyl (including the carbonyl from Y), e.g. prostaglandins such as prostaglandin $E_1$, as arachidonic acid derivatives are know regulators of hormone action including the action of prostaglandins, thromboxanes, and leukotrines. Examples of efficiency modifiers as $R^2$ are those which enhance the permeability of the target cell membrane as well as enhances the activity of extracellular $PLA_2$ or the active drug substance or any second drug substances. Examples hereof are short chain ($C_{8-12}$) fatty acids.

However, it is also envisaged that other groups might be useful as the organic radical $R^2$, e.g. vitamin D derivatives, steroid derivatives, retinoic acid (including all-trans-retinoic acid, all-cis-retinoic acid, 9-cis-retinoic acid, 13-cis-retinoic acid), cholecalciferol and tocopherol analogues, pharmacologically active carboxylic acids such as branched-chain aliphatic carboxylic acids (e.g. valproic acid and those described in WO 99/02485), salicylic acids (e.g. acetylsalicylic acid), steroidal carboxylic acids (e.g. lysergic and isolysergic acids), monoheterocyclic carboxylic acids (e.g. nicotinic acid) and polyheterocyclic carboxylic acids (e.g. penicillins and cephalosporins), diclofenac, indomethacin, ibuprofen, naproxen, 6-methoxy-2-naphthylacetic acid.

It should be understood that the various examples of possible $R^2$ groups are referred to by the name of a discrete species, rather than the name of the radical. Furthermore, it should be understood that the possible examples may include the carbonyl group or oxy group of the bond via which the organic radical is linked to the lipid skeleton (corresponding to "Y" in the formula above). This will of course be appreciated by the person skilled in the art.

Even though it has not specifically been indicated in the general formula for the suitable examples of lipid derivatives to be used within the present invention, it should be understood that the glycol moiety of the lipid derivatives may be substituted, e.g. in order to modify the cleavage rate by extracellular $PLA_2$ or simply in order to modify the properties of the liposomes comprising the lipid derivatives.

Lipid Derivatives as Prodrugs

As described above, the present invention provides the use if a lipid-based delivery system for administration of an active drug substance selected from lysolipid derivatives, wherein the active drug substance is present in the lipid-based system in the form of a prodrug, said prodrug being a lipid derivative having (a) an aliphatic group of a length of at least 7 carbon atoms and an organic radical having at least 7 carbon atoms, and (b) a hydrophilic moiety, said prodrug furthermore being a substrate for extracellular phospholipase A2 to the extent that the organic radical can be hydrolytically cleaved off, whereas the aliphatic group remains substantially unaffected, whereby the active drug substance is liberated in the form of a lysolipid derivative which is not a substrate for lysophospholipase for the treatment and/or prevention of parasitic infections in mammals.

Typical parasitic infections in mammals are those where the liver, spleen and bone marrow is targeted.

By the term "active drug substance" is meant any chemical entity which will provide a prophylactic or therapeutic effect in the body of a mammal, in particular a human.

The term "prodrug" should be understood in the normal sense, namely as a drug which is masked or protected with the purpose of being converted (typically by cleavage, but also by in vivo chemical conversion) to the intended drug substance. The person skilled in the art will recognise the scope of the term "prodrug".

The active drug substance is selected from lysolipid derivatives, and as it will be understood from the present description with claims, the lysolipid derivatives will have a therapeutic effect—at least—in connection with parasitic infections where a local area of the body of the mammal has a level of extracellular $PLA_2$ activity caused by said parasitic infection which can liberate the lysolipid derivative.

As will be understood from the present description with claims, the lipid derivative will often constitute the prodrug referred to above and the lysolipid derivative will thereby constitute the active drug substance often a monoether lysolipid derivative. It should however be understood that this does not exclude the possibility of including other drug substances, referred to as second drug substances, in the lipid-based delivery systems, neither does it exclude that the organic radical which can be hydrolytically cleaved by the action of extracellular $PLA_2$ can have a certain pharmaceutical effect (e.g. as an auxiliary drug substance or an efficiency modifier as described elsewhere herein) or act as a label. Furthermore, the pharmaceutical effect of the "active drug substance", i.e. the lysolipid derivative, need not the be the most predominant when a second drug substance is included, actually the effect of the second drug substance might very well be the most predominant as will become apparent in the other main embodiment (see "Lipid derivative liposomes as drug delivery systems", below).

The active drug substance (lipolipid derivative) release from the prodrug (lipid derivative) is believed to take place as illustrated in the following example:

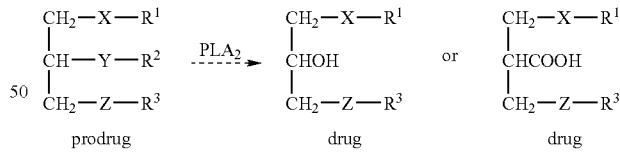

Furthermore, the substituent $R^2$ may constitute an auxiliary drug substance or an efficiency modifier for the active drug substance and will simultaneously be released under the action of extracellular $PLA_2$:

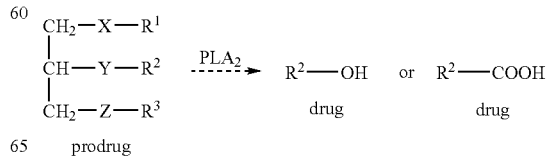

It has been described above under the definition of $R^2$ how the group $R^2$ can have various independent or synergistic effects in association with the active drug substance, e.g. as an auxiliary drug substance or an efficiency modifier, e.g. permeability or cell lysis modifier. It should be borne in mind that the groups corresponding to $R^2$ (e.g. $R^2$—OH or $R^2$—COOH) might have a pharmaceutical effect which is predominant in relation the effect of the lysolipid derivative (active drug substance).

Lipid Derivatives Formulated as Liposomes and Micelles

The term "lipid-based drug delivery system" should encompass macromolecular structures which as the main constituent include lipid or lipid derivatives. Suitable examples hereof are liposomes and micelles. It is presently believed that liposomes offer the broadest scope of applications and those have been described most detailed in the following. Although liposomes currently are believed to be the preferred lipid-based system, micellular systems are also believed to offer interesting embodiments within the present invention.

When used herein, the term "label" is intended to mean a species which is capable of being administered to the mammalian body and being detected by extracorporal means for imaging living tissue. The label may be selected from radiolabels such as radioisotopes and radioisotope-labeled compounds; radiopaque compounds; fluorescent compounds, etc. More specific labels are $^{111}$In, $^{99m}$Tc, $^{67}$Ga, $^{11}$C; Gd, Mn, iron oxide, argon, nitrogen, Iodine, bromine and barium.

Suitable labels for gamma-scintigraphy are diagnostic radionuclides, such as $^{111}$In, $^{99m}$Tc, $^{67}$Ga. For practical purposes the radionucleotides are complexed with e.g. chelators such as diethylene triamine pentaacetic acid (DTPA), hexamethylpropyleneamine oxime (HMPAO), diisopropyl iminodiacetic acid (DISIDA), or even proteins such as human serum albumin (HSA). Alternatively DTPA or similar chelating compounds may be derivatized by the incorporation of a hydrophobic group, which can anchor the chelating moiety on the liposome surface during or after liposome preparation.

Suitable labels for X-ray are verografin, ioxaglate, iohexol, iopromide, iomeprol, iopamidol, iopentol, iodixanol, ioversol different nonionic contrast media, etc. which may be incorporated in liposomes and used both for planar X-ray imaging of the liver and spleen and for CT imaging.

Suitable labels for magnetic resonance (MR) imaging are paramagnetic ions, such as Gd and Mn, and iron oxide coupled to various carrier molecules. E. g. gadolinium diethylenetriamine pentaacetic acid (Gd-DTPA) complex has been demonstrated to be effective contrast agents for MR imaging of liver, spleen, and hepatic metastases.

Suitable labels for computed tomography (CT) imaging are iodine, bromine, barium, etc.

Other examples of suitable labels are often given by the selected method of imaging or detection, examples of which are described in detail in Handbook of Medical Imaging, Vol. 1, 2 and 3, SPIE Press, Washington USA, 2000, eds. Beutel, Konden and van Metter.

The label can be adapted so as to be detectable and optionally quantifiable by a detection method selected from the group consisting of positron emission tomography (PET), X-ray, gamma-scintigraphy, magnetic resonance (MR) imaging, computed tomography (CT) imaging and ultrasonography.

Thus, the present invention also relates to an image enhancing systems (liposomes or micelles) for use in the present invention relies on lipid derivative having (a) an aliphatic group of a length of at least 7 carbon atoms and an organic radical having at least 7 carbon atoms, and (b) a hydrophilic moiety, said lipid-conjugated contrast agents furthermore being a substrate for extracellular phospholipase A2 to the extent that the organic radical can be hydrolytically cleaved off, whereas the aliphatic group remains substantially unaffected, whereby the lipid-conjugated contrast agents is liberated in the form of a lysolipid derivative which is not a substrate for lysophospholipase.

In one important variant which advantageously can be combined with the embodiments described herein, the lipid derivative (e.g. the prodrug) is included in liposomes either as the only constituent or—which is more common—in combination with other constituents (other lipids, sterols, etc.). Thus, the lipid-based systems described herein are preferably in the form of liposomes, wherein the liposomes are build up of layers comprising the lipid derivative (e.g. a prodrug).

"Liposomes" are known as self-assembling structures comprising one or more lipid bilayers, each of which surrounds an aqueous compartment and comprises two opposing monolayers of amphipathic lipid molecules. Amphipathic lipids (herein i.a. lipid derivatives) comprise a polar (hydrophilic) headgroup region (corresponding to the substituent $R^3$ in the lipid derivatives) covalently linked to one or two non-polar (hydrophobic) aliphatic groups (corresponding to $R^1$ and $R^2$ in the lipid derivatives). Energetically unfavourable contacts between the hydrophobic groups and the aqueous medium are generally believed to induce lipid molecules to rearrange such that the polar headgroups are oriented towards the aqueous medium while the hydrophobic groups reorient towards the interior of the bilayer. An energetically stable structure is formed in which the hydrophobic groups are effectively shielded from coming into contact with the aqueous medium.

Liposomes can have a single lipid bilayer (unilamellar liposomes, "ULVs"), or multiple lipid bilayers (multilamellar liposomes, "MLVs"), and can be made by a variety of methods (for a review, see, for example, Deamer and Uster, Liposomes, Marcel Dekker, N.Y., 1983, 27–52). These methods include Bangham's methods for making multilamellar liposomes (MLVs); Lenk's, Fountain's and Cullis' methods for making MLVs with substantially equal interlamellar solute distribution (see, e.g., U.S. Pat. No. 4,522,803, U.S. Pat. No. 4,588,578, U.S. Pat. No. 5,030,453, U.S. Pat. No. 5,169,637 and U.S. Pat. No. 4,975,282); and Papahadjopoulos et al.'s reverse-phase evaporation method (U.S. Pat. No. 4,235,871) for preparing oligolamellar liposomes. ULVs can be produced from MLVs by such methods as sonication (see Papahadjopoulos et al., Biochem. Biophys. Acta, 135, 624 (1968)) or extrusion (U.S. Pat. No. 5,008,050 and U.S. Pat. No. 5,059,421). The liposome can be produced by the methods of any of these disclosures, the contents of which are incorporated herein by reference.

Various methodologies, such as sonication, homogenisation, French Press application and milling can be used to prepare liposomes of a smaller size from larger liposomes. Extrusion (see U.S. Pat. No. 5,008,050) can be used to size reduce liposomes, that is to produce liposomes having a predetermined mean size by forcing the liposomes, under pressure, through filter pores of a defined, selected size. Tangential flow filtration (see WO 89/08846), can also be used to regularise the size of liposomes, that is, to produce liposomes having a population of liposomes having less size heterogeneity, and a more homogeneous, defined size distribution. The contents of these documents are incorporated herein by reference. Liposome sizes can also be determined by a number of techniques, such as quasi-electric light scattering, and with equipment, e.g., Nicomp® particle sizers, well within the possession of ordinarily skilled artisans.

It is quite interesting to note that the lipid derivatives can constitute the major part of a lipid-based system even if this system is a liposome system. This fact resides in the structural (but not functional) similarity between the lipid derivatives and lipids. Thus, it is believed that the lipid derivatives can be the sole constituent of liposomes, i.e. up to 100 mol % of the total dehydrated liposomes can be constituted by the lipid derivatives. This is in contrast to the known mono-ether lysolipides, which can only constitute a minor part of the liposomes.

Typically, as will be described in detail below, liposomes advantageously include other constituents which may or may not have a pharmaceutical effect, but which will render the liposome structure more stable (or alternatively more unstable) or will protect the liposomes against clearance and will thereby increase the circulation time thereby improving the overall efficiency of a pharmaceutical including the liposome. The liposomes may also include co-factors such as calcium, which upon release would increase $PLA_2$ activity, as well as lyso-lipids, fatty acids which are known to increase $PLA_2$ activity.

This being said, it is believed that the particular lipid derivatives will typically constitute from 15–100 mol %, such as 50–100 mol %, preferably from 75–100 mol %, in particular 90–100 mol %, based on the total dehydrated liposome.

The liposomes can be unilamellar or multilamellar. Some preferred liposomes are unilamellar and have diameters of less than about 200 nm, more preferably, from greater than about 50 nm to less than about 200 nm.

The liposomes are typically—as known in the art— prepared by a method comprising the steps of: (a) dissolving the lipid derivative in an organic solvent; (b) removing the organic solvent from the lipid derivative solution of step (a); and (c) hydrating the product of step (b) with an aqueous solvent so as to form liposomes.

The method may further comprise a step of adding an second substance (see below) to the organic solvent of step (a) or the aqueous phase of step (c).

Subsequently, the method may comprise a step of extruding the liposomes produced in step (c) through a filter to produce liposomes of a certain size, e.g. 100 nm.

The liposomes comprising lipid derivatives may (in principle) exclusively consist of the lipid derivatives. However, in order to modify the liposomes, "other lipids" may be included as well. Other lipids are selected for their ability to adapt compatible packing conformations with the lipid derivative components of the bilayer such that the all the lipid constituents are tightly packed, and release of the lipid derivatives from the bilayer is inhibited. Lipid-based factors contributing to compatible packing conformations are well known to ordinarily skilled artisans and include, without limitation, acyl chain length and degree of unsaturation, as well as the headgroup size and charge. Accordingly, suitable other lipids, including various phosphatidylethanolamines ("PE's") such as egg phosphatidylethanolamine ("EPE") or dioleoyl phosphatidylethanolamine ("DOPE"), can be selected by ordinarily skilled artisans without undue experimentation. Lipids may be modified in various way, e.g. by headgroup derivatisation with dicarboxylic acids, such as glutaric, sebacic, succinic and tartaric acids, preferably the dicarboxylic acid is glutaric acid ("GA"). Accordingly, suitable headgroup-derivatised lipids include phosphatidylethanolamine-dicarboxylic acids such as dipalmitoyl phosphatidylethanolamine-glutaric acid ("DPPE-GA"), palmitoyloleoyl phosphatidylethanolamine-glutaric acid ("POPE-GA") and dioleoyl phosphatidylethanolamine-glutaric acid ("DOPE-GA"). Most preferably, the derivatised lipid is DOPE-GA.

The total content of "other lipids" will typically be in the range of 0–30 mol %, in particular 1–10 mol %, based on the total dehydrated liposome.

Sterolic compound included in the liposome may generally affects the fluidity of lipid bilayers. Accordingly, sterol interactions with surrounding hydrocarbon groups generally inhibit emigration of these groups from the bilayer. An examples of a sterolic compound (sterol) to be included in the liposome is cholesterol, but a variety of other sterolic compounds are possible. It is generally believed that the content of sterolic compound, if present, will be in the range of 0–25 mol %, in particular 0–10 mol %, such as 0–5 mol %, based on the total dehydrated liposome.

Although the an element of idea on which the present invention resides is that the liposomes or micelles should be taken up by the RES system, it may be advantageous to include a small fraction of lipids or lipid derivatives on which polymeric chains are attached in order to adjust the rate at which the liposomes and micelles are taken up and thereby degraded. Thus, is may be advantageous to partially, but not fully, employ the so-called STEALTH® liposomes (Liposome Technology Inc., Menlo Park, Calif.) which include polyethyleneglycol (PEG)-grafted lipids at about 5 mol % of the total dehydrated liposome, or other lipopolymers carrying hydrophilic polymer chains. The presence of such polymers on the exterior liposome surface should slightly delay, but not prevent, the uptake of liposomes by the organs of the RES. If present, the lipopolymers typically constitute 0.1–10 mol % of the total dehydrated system.

Hydrophilic polymers suitable for use in lipopolymers are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilises polymers of at least about three monomers, such PEG polymers consisting of three monomers (approximately 150 daltons). Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatised celluloses such as hydroxymethylcellulose or hydroxyethylcellulose.

Glycolipids are lipids to which a hydrophilic polysaccharide chain is covalently attached. It will be appreciated that glycolipids can be utilised like lipopolymers although the lipopolymers currently presents the most promising results.

It is generally believed that the content of lipopolymer, i present, advantageously will be in the range of 0.1–5 mol %, such as 0.2–4 mol %, in particular 0.5–3 mol %, based on the total dehydrated liposome.

Still other ingredients may constitute 0–2 mol %, in particular 0–1 mol %, based on the total dehydrated liposome.

According to an embodiment, the lipid bilayer of a liposome contains lipids derivatised with polyethylene glycol (PEG), such that the PEG chains extend from the inner surface of the lipid bilayer into the interior space encapsulated by the liposome, and extend from the exterior of the lipid bilayer into the surrounding environment (see e.g. U.S. Pat. No. 5,882,679).

The liposome can be dehydrated, stored and then reconstituted such that a substantial portion of its internal contents is retained. Liposomal dehydration generally requires use of a hydrophilic drying protectant such as a disaccharide sugar at both the inside and outside surfaces of the liposome bilayers (see U.S. Pat. No. 4,880,635). This hydrophilic compound is generally believed to prevent the rearrangement of the lipids in the liposome, so that the size and contents are maintained during the drying procedure and through subsequent rehydration. Appropriate qualities for such drying protectants are that they are strong hydrogen bond acceptors, and possess stereochemical features that preserve the intramolecular spacing of the liposome bilayer components. Alternatively, the drying protectant can be omitted if the liposome preparation is not frozen prior to dehydration, and sufficient water remains in the preparation subsequent to dehydration.

Lipid Derivative Liposomes as Drug or Label Carrier Systems

As mentioned above, the liposomes including the lipid derivatives may also include second substances, where such second substances may be drugs or labels. In a particular embodiment, the lipid-based delivery system described above is in the form of liposomes wherein a second substance is incorporated. It should be understood that second drug substances may comprise pharmaceutically active ingredients which may have an individual or synergistic pharmaceutical effect in combination with the lipid derivative and lysolipid derivatives. Furthermore, that when the second substance is a label, said label may comprise contrast substances or other substances detectable by means of MR, CT, Gamma-scintigraphy or ultrasonography. The term "second" does not necessarily imply that the pharmaceutical effect of the second drug substance is inferior in relation to that of, e.g., the active drug substance derived from the prodrug, but is merely used to differentiate between the two groups of substances.

This being said, the present invention also provides the use of a delivery system which is in the form of liposomes, and wherein a second substance is incorporated, either as a drug or as a label.

A possible "second drug substance" is any compound or composition of matter that can be administered to mammals, preferably humans. Such agents can have biological activity in mammals. Second drug substances which may be associated with liposomes are well known anti-paracitic compounds, such as allopurinol, amodiaquine, amphotericin, antifolates, artemether+benflumetol, artemisinin, derivatives, chloroproguanil, Chloroquine, combination of atovaquone and proguanil HCL (salesname Malarone™), dapsone, Doxycycline, halofantrine, interferon gamma, Licochocone A, Mefloquine, meglumine antimonate, metronidazole, nitrofurantoin derivatives, paromomycin, pentamidine, primaquine, primaquine, Proguanil, (Chloroquine plus proguanil), puromycin, pyrimethamine, pyronaridine, quinine and sodium stibogluconate.

Liposomal second drug substance formulations enhance the therapeutic index of the second drug substances by reducing the toxicity of the drug. Liposomes can also reduce the rate at which a second drug substance is cleared from the vascular circulation of mammals. Accordingly, liposomal formulation of second drug substance can mean that less of the drug need be administered to achieve the desired effect.

Liposomes can be loaded with one or more second substances by solubilising the drug or label in the lipid or aqueous phase used to prepare the liposomes. Alternatively, ionisable second substances can be loaded into liposomes by first forming the liposomes, establishing an electrochemical potential, e.g., by way of a pH gradient, across the outermost liposomal bilayer, and then adding the ionisable second substance to the aqueous medium external to the liposome (see, e.g., U.S. Pat. No. 5,077,056 and WO 86/01102).

Methods of preparing lipophilic drug or label derivatives which are suitable for liposome or micelle formulation are known in the art (see e.g., U.S. Pat. No. 5,534,499 and U.S. Pat. No. 6,118,011 describing covalent attachment of therapeutic agents to a fatty acid chain of a phospholipid). A micellar formulation of taxol is described in Alkan-Onkyuksel et al., Pharmaceutical Research, 11:206 (1994).

Accordingly, the second drug substance may be any of a wide variety of known and possible pharmaceutically active ingredients, but is preferably a therapeutically and/or prophylactically active substance. Due to the mechanism involved in the degradation of the liposomes, it is preferred that the second drug substance is one relating to diseases and/or conditions associated with a localised increase in extracellular $PLA_2$ activity.

It is envisaged that the second substance will be distributed in the liposomes according to their hydrophilicity, i.e. hydrophilic second substances will tend to be present in the cavity of the liposomes and hydrophobic second substances will tend to be present in the hydrophobic bilayer. Method for incorporation of second substances are know in the art as has been made clear above.

It should be understood from the above, that the lipid derivatives may—as prodrugs or discrete constituents—posses a pharmaceutical or diagnostic activity. However, in a particular embodiment, the present invention furthermore relates to a lipid based drug or label delivery system for administration of an second substance, wherein the second substance is incorporated in the system (e.g. where the second substance is encapsulated in the interior of the liposome or in the membrane part of the liposome or the core region of micelle), said system including lipid derivatives which has (a) an aliphatic group of a length of at least 7 carbon atoms and an organic radical having at least 7 carbon atoms, and (b) a hydrophilic moiety, where the lipid derivative furthermore is a substrate for extracellular phospholipase A2 to the extent that the organic radical can be hydrolytically cleaved off, whereas the aliphatic group remains substantially unaffected, so as to result in an organic acid fragment or an organic alcohol fragment and a lysolipid fragment, said lysolipid fragment not being a substrate for lysophospholipase.

As above for the system according to the other embodiment, the organic radical which can be hydrolytically cleaved off, may be an auxiliary drug or label substance or an efficiency modifier for the second substance. It should be understood that the lipid derivative is a lipid derivative as defined further above. Typically, the lipid derivative constitutes 15–100 mol %, such as 50–100 mol %, of the total dehydrated (liposome) system.

The present invention relates to the use of any of the lipid-based drug delivery systems described herein for the preparation of a medicament for the treatment of parasitic infections of a mammal, wherein the parasitic infection is characterized by increasing the level of $PLA_2$ in said mammal, particularly in the specific tissue of infection, preferably of the liver or spleen.

Furthermore, the present invention relates to the use of any of the lipid-based delivery systems described herein for the preparation of a diagnostic agent for the detection or quantification of parasitic infections of a mammal, wherein the parasitic infection is characterized by increasing the level of $PLA_2$ in said mammal, particularly in the specific tissue of infection, preferably of the liver or spleen.

Pharmaceutical Preparations and Therapeutic Uses

"Pharmaceutically acceptable carriers" as used herein are those media generally acceptable for use in connection with the administration of lipids and liposomes, including liposomal drug formulations, to mammals, including humans. Pharmaceutically acceptable carriers are generally formulated according to a number of factors well within the purview of the ordinarily skilled artisan to determine and account for, including without limitation: the particular active drug substance and/or second drug or label substance used, the liposome preparation, its concentration, stability and intended bioavailability; the disease, disorder or condition being treated with the liposomal composition; the subject, its age, size and general condition; and the composition's intended route of administration, e.g., nasal, oral, ophthalmic, subcutaneous, intramammary, intraperitoneal, intravenous, or intramuscular. Typical pharmaceutically acceptable carriers used in parenteral drug administration include, for example, D5W, an aqueous solution containing 5% weight by volume of dextrose, and physiological saline. Pharmaceutically acceptable carriers can contain additional ingredients, for example those which enhance the stability of the active ingredients included, such as preservatives and anti-oxidants.

The liposome or lipid derivative is typically formulated in a dispersion medium, e.g. a pharmaceutically acceptable aqueous medium.

An amount of the composition comprising an anti-parasitic effective amount of the lipid derivative, typically from about 0.1 to about 1000 mg of the lipid derivative per kg of the mammal's body, is administered, preferably intravenously. For the purposes of this invention, "anti-parasitic effective amounts" of liposomal lipid derivatives are amounts effective to inhibit, ameliorate, lessen or prevent establishment, proliferation, growth, etc. of parasites in mammals to which the lipid derivatives have been administered. Anti-parasitic effective amounts are generally chosen in accordance with a number of factors, e.g., the age, size and general condition of the subject, the parasitic infection being treated and the intended route of administration, and determined by a variety of means, for example, dose ranging trials, well known to, and readily practised by, ordinarily skilled artisans given the teachings of this invention. Anti-parasitic effective amounts of the liposomal drugs/prodrugs of this invention are about the same as such amounts of free, nonliposomal, drugs/prodrugs, e.g., from about 0.1 mg of the lipid derivative per kg of body weight of the mammal being treated to about 1000 mg per kg. The pharmaceutical composition is preferably administered parenterally by injection, infusion or implantation (intravenous, intramuscular, intraarticular, subcutaneous or the like) in dosage forms, formulations or e.g. suitable delivery devices or implants containing conventional, non-toxic pharmaceutically acceptable carriers and adjuvants.

The formulation and preparation of such compositions is well-known to those skilled in the art of pharmaceutical formulation. Specific formulations can be found in the textbook entitled "Remington's Pharmaceutical Sciences".

Thus, the pharmaceutical compositions may comprise the active substances in the form of a sterile injection. To prepare such a composition, the suitable active substances are dispersed in a parenterally acceptable liquid vehicle which conveniently may comprise suspending, solubilising, stabilising, pH-adjusting agents and/or dispersing agents. Among acceptable vehicles that may be employed are water, water adjusted to a suitable pH by addition of an appropriate amount of hydrochloric acid, sodium hydroxide or a suitable buffer, 1,3-butanediol, Ringer's solution and isotonic sodium chloride solution.

The aqueous formulation may also contain one or more preservatives, for example, methyl, ethyl or n-propyl p-hydroxybenzoate.

Toxicity

Toxicity of the liposomes comprising the lipid derivatives can be assessed by determining the therapeutic window "TW", which is a numerical value derived from the relationship between the compound's induction of hemolysis and its ability to inhibit the growth/proliferation of parasites. TW values are defined as $HI_5/GI_{50}$ (wherein "$HI_5$" equals the concentration of compound inducing the hemolysis of 5% of the red blood cells in a culture, and wherein "$GI_{50}$" equals the dose of compound inducing fifty percent growth inhibition in a population of parasitic cells exposed to the agent). The higher an agent's $HI_5$ value, the less hemolytic is the agent—higher $HI_5$'s mean that greater concentrations of compound are required to be present in order for the compound to induce 5% hemolysis. Hence, the higher its $HI_5$, the more therapeutically beneficial is a compound, because more of it can be given before inducing the same amount of hemolysis as an agent with a lower $HI_5$. By contrast, lower $GI_{50}$'s indicate better therapeutic agents—a lower $GI_{50}$ value indicates that a lesser concentration of an agent is required for 50% growth inhibition. Accordingly, the higher is its $HI_5$ value and the lower is its $GI_{50}$ value, the better are a compound's agent's therapeutic properties.

Generally, when a drug's TW is less than 1, it cannot be used effectively as a therapeutic agent. That is, the agent's $HI_5$ value is sufficiently low, and its $GI_{50}$ value sufficiently high, that it is generally not possible to administer enough of the agent to achieve a sufficient level of parasite growth inhibition without also attaining an unacceptable level of hemolysis. As the lipid derivative liposomes take advantage of the lower extracellular $PLA_2$ activity in the bloodstream compared to the activity in the diseased tissue, it is believed that the TW will be much higher that for normal monoether lysolipids. As the variance in activity is in orders of magnitude and as the liposomes will be "trapped" in tissue with a high extracellular $PLA_2$ activity, it is generally believed the TW of the liposomes of the invention will be greater than about 3, more preferably greater than about 5, and still more preferably greater than about 8.

The invention will be illustrated by the following non-limiting examples.

EXAMPLES

Example 1

Liposome Preparation

Unilamellar fully hydrated liposomes with a narrow size distribution were made from 1-O-hexadecyl-2-hexadecanoyl-sn-glycero-3-phosphocholine (1-O-DPPC) and di-hexa-decanoyl-sn-glycero-3-phosphocholine (DPPC). DPPC were obtained from Avanti Polar lipids and 1-O-DPPC were synthesised in our laboratory. Briefly, weighed amounts of DPPC or 1-O-DPPC were dissolved in chloroform. The solvent was removed by a gentle stream of $N_2$ and the lipid films were dried overnight under low pressure to remove trace amounts of solvent. Multilamellar vesicles were made by dispersing the dried lipids in a buffer solution containing: 150 mM KCL, 10 mM HEPES (pH=7.5), 1 mM $NaN_3$, 30 μM $CaCl_2$ and 10 μM EDTA. The multilamellar vesicles were extruded ten times through two stacked 100 nm pore size polycarbonate filters as described by Mayer et al., *Biochim. Biophys. Acta*, 858, 161–168.

Heat capacity curves were obtained using a N-DSC II differential scanning calorimeter (Calorimetry Sciences Corp., Provo) of the power compensating type with a cell volume of 0.34 mL. Before scanning, the liposome suspension was equilibrated for 50 min in the calorimeter at the starting temperature. A scan rate of +10° C./h was used. The lipid concentration was 1 mM. The gel-to-fluid transition of the multilamellar liposomes (MLV) is characterised as a sharp first-order transition, as reflected by the narrow peak in the heat capacity curves shown in FIGS. 1*a* and 1*b* (upper curves) for 1-O-DPPC and DPPC. The sharp peak reflects the transitional behavior of multilamellar liposomes and is in contrast to the broader gel-to-fluid transition observed for unilamellar liposomes (LUV) (Pedersen et al., 1996, *Biophys. J.* 71, 554–560) as shown in FIGS. 1*a* and 1*b* (lower curves) for the unilamellar extruded 1-O-DPPC and DPPC liposomes.

Example 2

Phospholipase $A_2$ Reaction Profile and Lag Time Measurements

Purified snake-venom phospholipase $A_2$ ($PLA_2$ from Agikistrodon piscivorus piscivorus) has been isolated according to the procedure of Maraganore et al., *J. Biol. Chem.* 259, 13839–13843. This $PLA_2$ enzyme belongs to the class of low-molecular weight 14 kD secretory enzymes which display structural similarity to human extracellular phospholipase $A_2$ indicating a common molecular mechanisms of the phospholipase catalysed hydrolysis at the lipid-membrane interface (Wery et al., *Nature* 352, 79–82; Honger et al. *Biochemistry* 35, 9003–9006; Vermehren et al., *Biochimica et Biophysica Acta* 1373, 27–36). Unilamellar fully hydrated liposomes with a narrow size distribution were prepared from 1-O-hexadecyl-2-hexadecanoyl-sn-glycero-3-phosphocholine (1-O-DPPC) and from 1-O-DPPC with 5 mol % 1-O-hexadecyl-2-hexadecanoyl-sn-glycero-3-phosphoethanolamine-N-[methoxy(polyethylene glycol)-350] (1-O-DPPE-PEG350). Assay conditions for the $PLA_2$ reaction time profile shown in FIG. 2 and the lag-time and percent hydrolysis reported in Table 1 were: 0.15 mM unilamellar liposomes, 150 nM $PLA_2$, 150 mM KCL, 10 mM HEPES (pH 7.5), 1 mM $NaN_3$, 30 μM $CaCl_2$, and 10 μM EDTA.

TABLE 1

| Composition | Lag-time (sec) | 1-O-DPPC (%) |
|---|---|---|
| 100% 1-O-DPPC | 583 | 79 |
| 95% 1-O-DPPC/5% 1-O-DPPE-PEG350 | 128 | 73 |

Lag-time and percent hydrolysed 1-O-DPPC at 41° C. as determined by HPLC.
The lipid concentration was 0.150 mM in a 10 mM HEPES-buffer (pH = 7.5).

Figure 3:
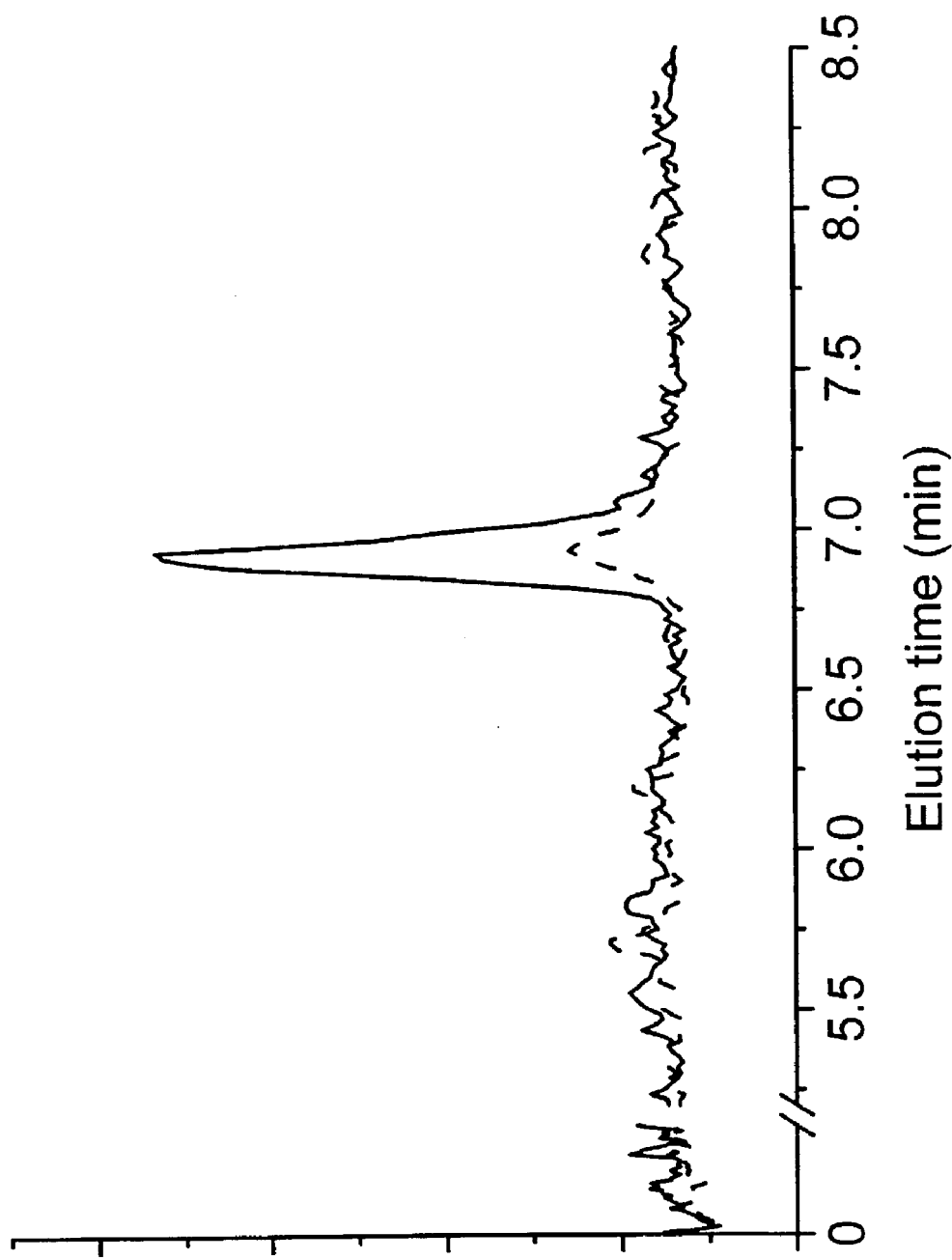
FIG. 3 HPLC chromatograms illustrating the effect of phospholipase $A_2$ hydrolysis of liposomes composed of 1-O-DPPC. The chromatograms show the amount of 1-O-DPPC (100%, solid line) before phospholipase $A_2$ (A. piscivorus piscivorus) was added to the liposome suspension and the amount of 1-O-DPPC (21%, dashed line) after the lag-burst.

The catalytic reaction was initiated by adding 8.9 μL of a 42 μM $PLA_2$ (150 nM) stock solution to 2.5 ml of the thermostated liposome suspension (0.150 mM) equilibrated for 800 sec prior to addition of $PLA_2$. The characteristic lag-burst behavior of $PLA_2$ towards the liposomes is signaled by a sudden increase in the intrinsic fluorescence from $PLA_2$ at 340 nm after excitation at 285 nm followed by a concomitant decrease in the 90° light scattering from the lipid suspension (Hønger et al., *Biochemistry* 35, 9003–9006). Samples for HPLC analysis of the amount of non-hydrolysed 1-O-DPPC remaining and consequently the amount of 1-O-hexadecyl-2-hydroxy-sn-glycero-3-phosphocholine (lyso-1-O-PPC) generated were taken before adding $PLA_2$ and 1200 sec after the observed lag-time. 100 μl aliquots were withdrawn from the lipid suspension and rapidly mixed with 1 ml chloroform/methanol/acetic acid (2:4:1) solution in order to quench the enzymatic reaction. The solution was washed with 1 ml of water and 20 μl of the heavy organic phase was used for HPLC. The HPLC chromatograms in FIG. 3 show the amounts of 1-O-DPPC before and after (t=3000 sec) the addition of $PLA_2$ (t=800 sec) to the liposome suspension. HPLC analysis was made using a 5 μm diol column, a mobile phase composed of chloroform/methanol/water (730:230:30, v/v) and an evaporative light scattering detector. The turnover of the $PLA_2$ catalysed lipid hydrolysis of 1-O-DPPC to lyso-1-O-DPPC was measured by HPLC (see Table 1). The intrinsic enzyme fluorescence and 90° light scattering were measured as a function of time as shown in FIG. 2.

Example 3

Phospholipase $A_2$ Induced Release of an Incapsulated Water-Soluble Model Drug

Multilamellar 1-O-DPPC-liposomes were made in the presence of fluorescent calcein in a self-quenching concentration of 20 mM by hydrating a film of 1-O-hexadecyl-2-hexadecanoyl-sn-glycero-3-phosphocholine in a HEPES buffer solution at pH=7.5 for one hour at 10° C. above the phase transition temperature. Unilamellar liposomes were formed by extruding the multilamellar liposomes ten times through two stacked 100 nm polycarbonate filters. The unilamellar liposomes were rapidly cooled to a temperature below the transition temperature, and the calcein-containing 1-O-DPPC liposomes were separated from free calcein using a chromatographic column packed with Sephadex G-50.

Figure 4:
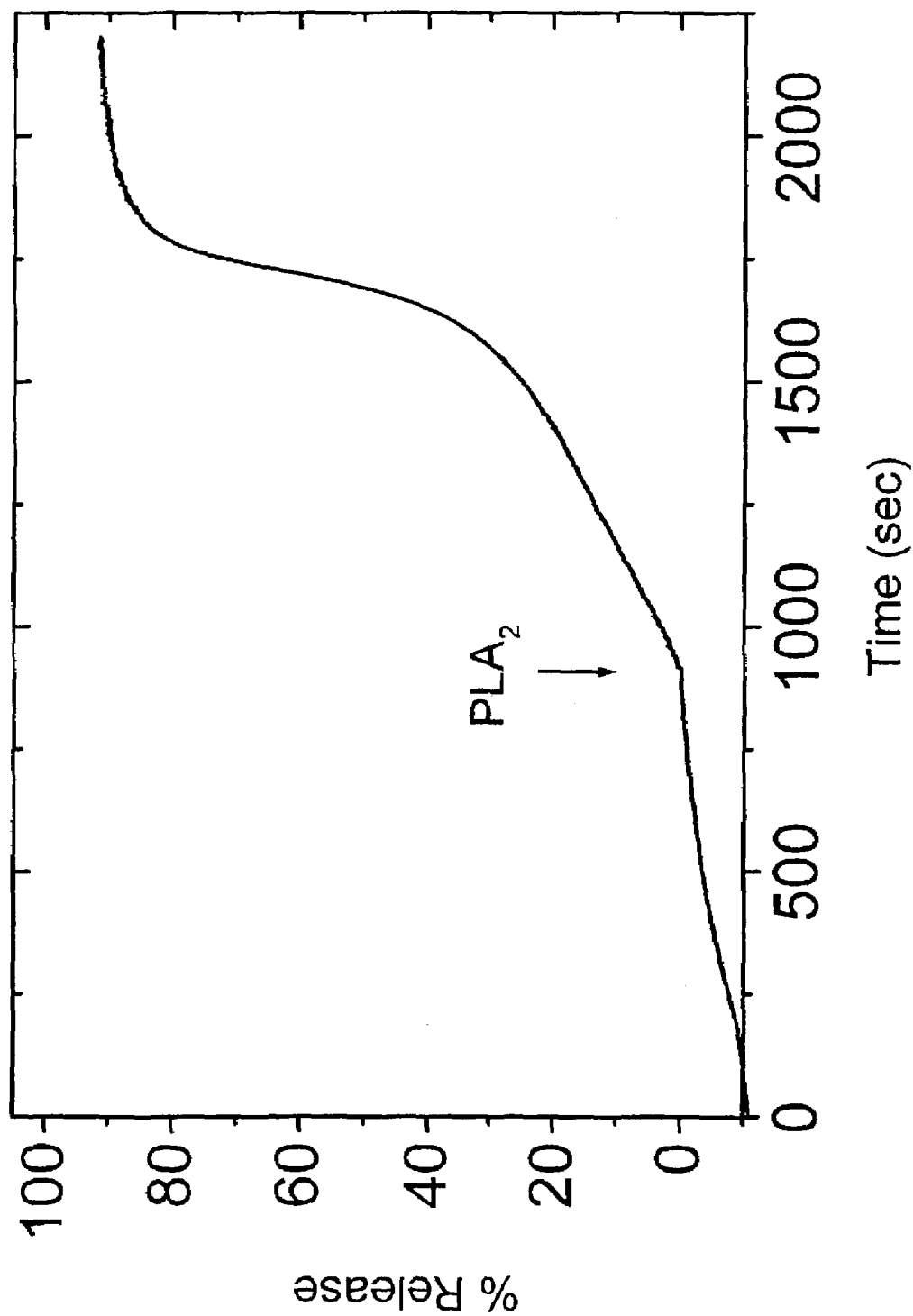
FIG. 4. PLA$_2$-controlled release of the fluorescent model drug calcein from liposomes composed of 25 μM 1-O-hexadecyl-2-hexadecanoyl-sn-glycero-3-phosphocholine (1-O-DPPC) suspended in a 10 mM HEPES-buffer (pH=7.5), as a function of time. 25 nM phospholipase A$_2$ (A. piscivorus piscivorus) was added at time 900 sec, the temperature was 37° C. The percentage of calcein released is determined as % Release=100 $(I_{F(t)}-I_B)/(I_T-I_B)$, where $I_{F(t)}$ is the measured fluorescence at time t after addition of the enzyme, $I_B$ is the background fluorescence, and $I_T$ is the total fluorescence measured after addition of Triton X-100 which leads to complete release of calcein by breaking up the liposomes.

Assay conditions for the $PLA_2$ induced calcein release were 25 μM unilamellar 1-O-DPPC-liposomes, 25 nM $PLA_2$, 150 mM KCL, 10 mM HEPES (pH 7.5 or 8.0), 1 mM $NaN_3$, 30 μM $CaCl_2$, and 10 μM EDTA. $PLA_2$ was added at time 900 sec to 2.5 ml of the thermostated 1-O-DPPC-liposome suspension equilibrated for at least 20 min at 37° C. prior to addition of $PLA_2$. The percentage of calcein released is determined as: % Release=$100 \times (I_{F(t)} - I_B)/(I_T - I_B)$, where $I_{F(t)}$ is the measured fluorescence at time t after addition of the enzyme, $I_B$ is the background fluorescence, and $I_T$ is the total fluorescence measured after addition of Triton X-100 which leads to complete release of calcein by breaking up the 1-O-DPPC-liposomes. $PLA_2$ induced at total release of 90 percent of the entrapped calcein in the 1-O-DPPC-liposomes as shown in FIG. 4.

Example 4

Phospholipase $A_2$ Controlled Permeability Increase of a Target Model Membrane

Multilamellar model membrane target liposomes were made in the presence of fluorescent calcein in a self-quenching concentration of 20 mM by hydrating a film of 1,2-O-dioctadecyl-sn-glycero-3-phosphatidylcholines (D-O-SPC) in a HEPES buffer solution at pH=7.5 for one hour at 10° C. above the phase transition temperature ($T_m$=55° C.).

Unilamellar liposomes were made by extruding the multilamellar target liposomes ten times through two stacked 100 nm polycarbonate filters. The unilamellar liposomes were rapidly cooled to a temperature below the transition temperature, and the calcein-containing liposomes were separated from free calcein using a chromatographic column packed with Sephadex G-50. The unilamellar carrier liposomes composed of 1-O-hexadecyl-2-hexadecanoyl-sn-glycero-3-phosphocholine were prepared as described above. Calcein release from the target liposomes is determined by measuring the fluorescent intensity at 520 nm after excitation at 492 nm.

Figure 5:
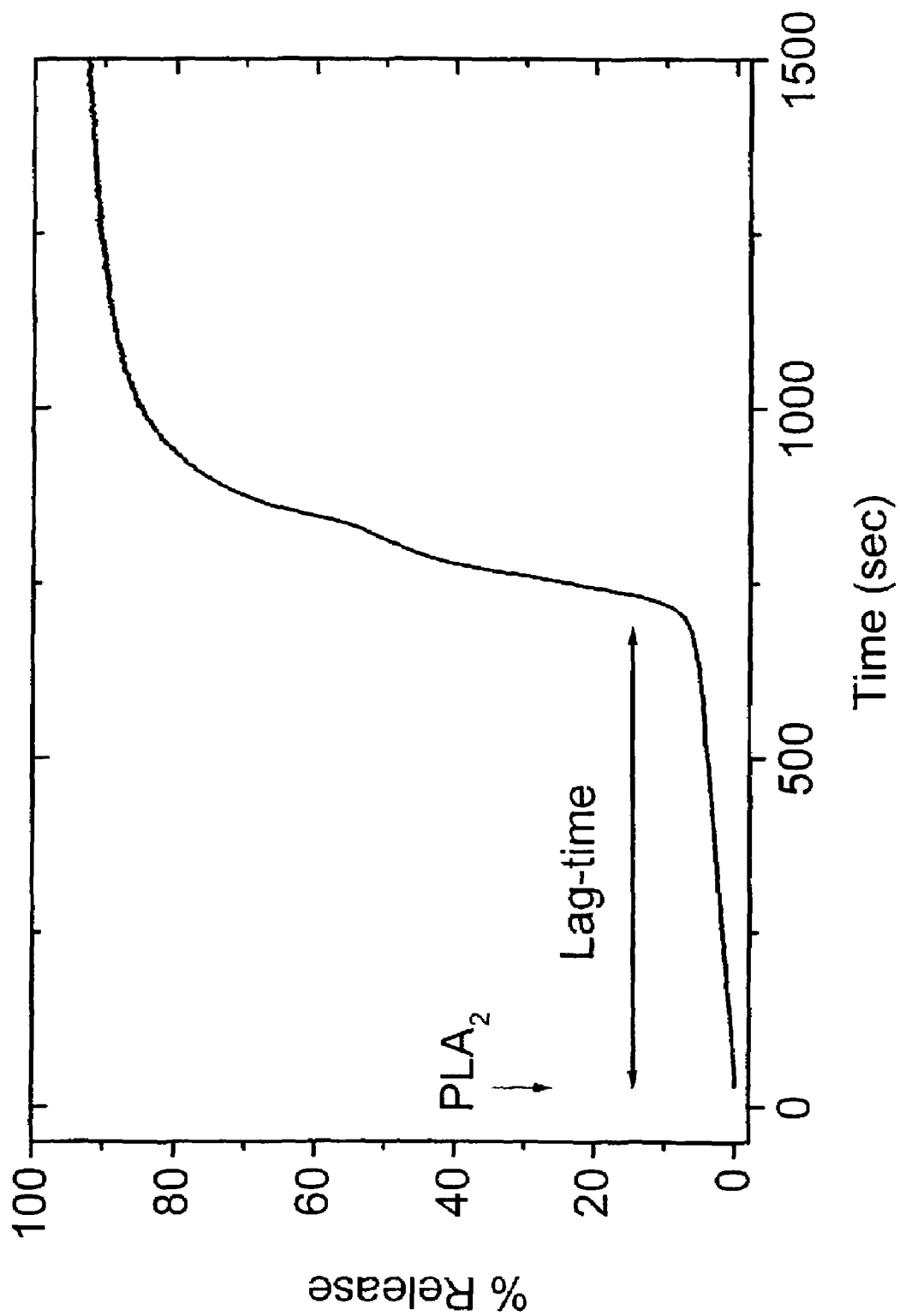
FIG. 5. PLA$_2$-controlled release of the fluorescent model drug calcein across the target membrane of non-hydrolysable membranes (see FIG. 11b), as a function of time for liposomes composed of 25 μM 1-O-hexadecyl-2-hexadecanoyl-sn-glycero-3-phosphocholine (1-O-DPPC) suspended in a 10 mM HEPES-buffer (pH=7.5). 25 nM phospholipase A$_2$ was added at time 0 sec and the temperature was 37° C. The percentage of calcein released is determined as described in FIG. 4.

The concentrations of D-O-SPC and 1-O-DPPC-liposomes were 25 µM. Snake venom $PLA_2$ (Agkistrodon piscivorus piscivorus) was added (25 nM) to initiate the hydrolytic reaction leading to the formation of 1-O-hexadecyl-2-hydroxy-sn-glycero-3-phosphocholine (lyso-1-O-DPPC) and fatty acid hydrolysis products. As calcein is released from the D-O-SPC liposomes, due to the incorporation of the non-bilayer forming lyso-1-O-PPC and fatty acid hydrolysis products into the target lipid membrane, a linear increase in the fluorescence at 520 nm after excitation at 492 nm is observed when calcein is diluted into the surrounding buffer medium as shown in FIG. 5. The percentage of calcein released is determined as described above (see Example 3).

Example 5

Hemolysis Assay

Unilamellar fully hydrated liposomes with a narrow size distribution were prepared from 1-O-hexadecyl-2-hexadecanoyl-sn-glycero-3-phosphocholine (1-O-DPPC), and from 1-O-DPPC with 5 mol % 1-O-hexadecyl-2-hexadecanoyl-sn-glycero-3-phosphoethanolamine-N-[methoxy(polyethylene glycol)-350] (1-O-DPPE-PEG350). The lipids were hydrated in phosphate buffered saline (PBS). 1-O-octadecyl-2-O-methyl-sn-glycero-3-phosphocholine (ET-18-OCH$_3$) in PBS was included in the assay as a reference.

Figure 6:
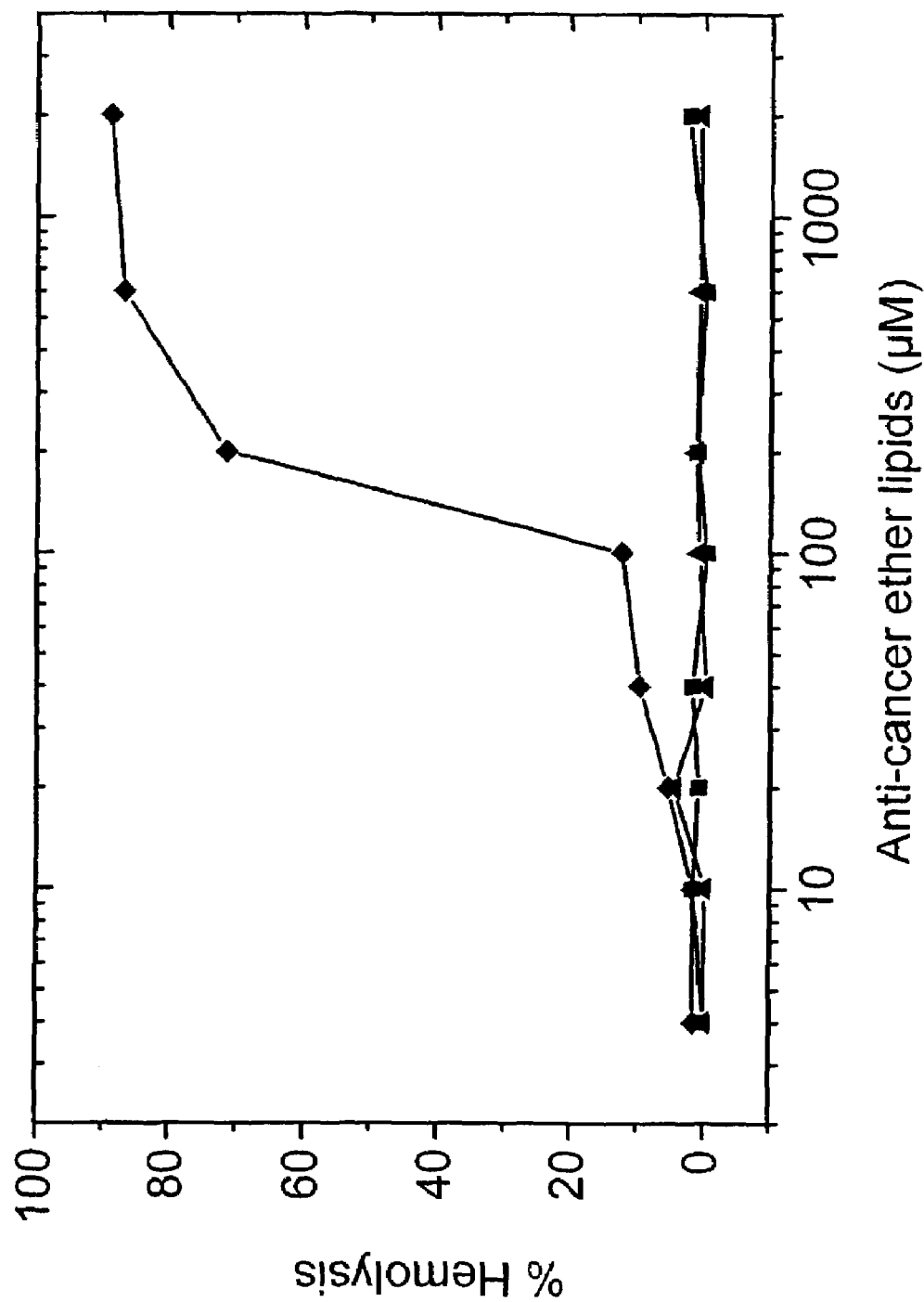
FIG. 6. Hemolysis profile of normal red blood cells in the presence of liposomes composed of 100% 1-O-DPPC (squares); 95% 1-O-DPPC and 5% negatively charged 1-O-hexadecyl-2-hexadecanoyl-sn-glycero-3-phosphoethanolamine-N-[methoxy(polyethylene glycol)-350] (1-O-DPPE-PEG350) (triangles) and 1-O-octadecyl-2-O-methyl-sn-glycero-3-phosphocholine (ET-18-OCH$_3$) (diamonds). The concentrations that yield 5% hemolysis ($H_5$) were well above 2 mM for liposomes composed of 100% 1-O-DPPC, and for liposomes composed of 90% 1-O-DPPC with 5% DPPE-PEG350. Hemolysis assay was performed as described by Perkins et al., 1997, Biochimica et Biophysica Acta 1327, 61–68. Briefly, each sample was serially diluted with phosphate buffered saline (PBS), and 0.5 ml of each dilute suspension was mixed with 0.5 ml washed human red blood cells (RBC) [4% in PBS (v/v)]. Sample and standard were placed in a 37° C. incubator and agitated for 20 hours. Tubes were centrifuged at low speed (2000×G) for 10 minutes and 200 μl of the supernatant was quantitated by absorbance at 550 nm. 100 percent hemolysis was defined as the maximum amount of hemolysis obtained from the detergent Triton X-100. The hemolysis profile in FIG. 6 shows a low hemolysis value (below 5% percent) for 2 mM 1-O-DPPC-liposomes and for 1-O-DPPC with 5% 1-O-DPPE-PEG350, liposomes.

Hemolysis assay was performed as described by Perkins et al., *Biochim. et Biophys. Acta* 1327, 61–68. Briefly, each sample was serially diluted with PBS, and 0.5 ml of each dilute suspension of 1-O-DPPC liposomes were mixed with 0.5 ml washed human red blood cells (RBC) [4% in PBS (v/v)]. For controls, 0.5 ml of the red blood cell suspension was mixed with either 0.5 ml buffer solution (negative hemolysis control) or 0.5 ml water (positive hemolysis control). Samples and standard were placed in a 37° C. incubator and agitated for 20 hours. Tubes were centrifuged at low speed (2000×G) for 10 minutes to form RBCs pellets. 200 µl of the supernatant was quantified by absorbance at 550 nm using a Perkin-Elmer 320 scanning spectrophotometer. 100 percent hemolysis was defined as the maximum amount of hemolysis obtained from the detergent Triton X-100. The hemolysis profile in FIG. 6 shows a low hemolysis value (below 5 percent) for 2 mM 1-O-DPPC-liposomes. FIG. 6 also shows that low concentrations of ET-18-OCH$_3$ induces a significant degree of hemolysis.

Example 6

Figure 7:
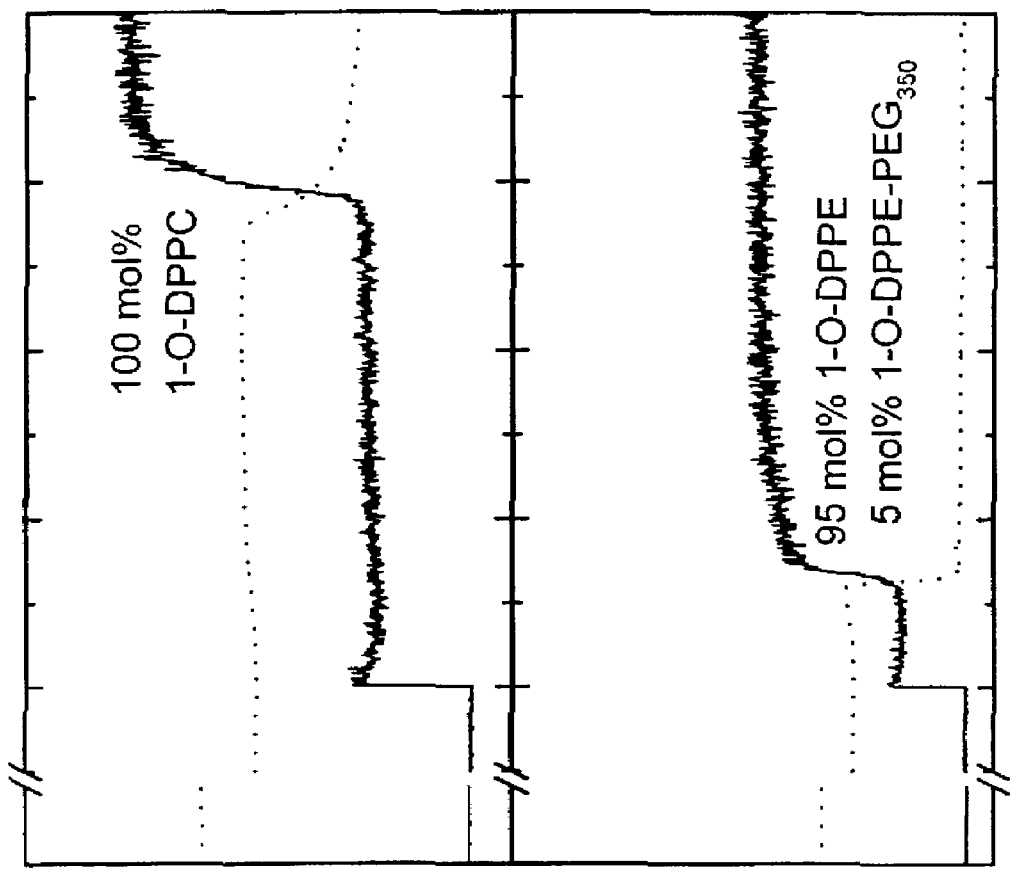
FIG. 7. Characteristic reaction time profiles at 41° C. for PLA$_2$ (A. piscivorus piscivorus) hydrolysis of unilamellar liposomes incorporated with 0 and 5% 1-O-DPPE-PEG350 lipopolymers. The PLA$_2$ hydrolysis reaction is monitored by intrinsic fluorescence (solid line) from the enzyme and 90° static light scattering (dashed lines) from the suspension. After adding PLA$_2$ to the equilibrated liposome suspension a characteristic lag-time follows before a sudden increase in the catalytic activity takes place.

Enhancement of Phospholipase A2 Activity by Negatively Charged Polymer Grafted 1-O-Lipids Unilamellar fully hydrated liposomes with a narrow size distribution were prepared from 1-O-hexadecyl-2-hexadecanoyl-sn-glycero-3-phosphocholine (1-O-DPPC) and 1-O-DPPC with 5 mol % 1-O-hexadecyl-2-hexadecanoyl-sn-glycero-3-phosphoethanolamine-N-[methoxy(polyethylene glycol)-350] (1-O-DPPE-PEG350), as described in example 2. Assay conditions for the $PLA_2$ lag-time measurements were 0.15 mM unilamellar liposomes, 150 nM $PLA_2$, 150 mM KCL, 10 mM HEPES (pH 7.5), 1 mM NaN$_3$, 30 µM CaCl$_2$, and 10 µM EDTA. The catalytic reaction was initiated by adding 8.9 µL of a 42 µM $PLA_2$ stock solution to 2.5 ml of the thermostated liposomes suspension equilibrated for 800 seconds at 41° C. prior to addition of $PLA_2$. The time elapsed before the onset of rapid enzymatic activity is determined by a sudden increase in the intrinsic fluorescence from $PLA_2$ at 340 nm after excitation at 285 nm. The results shown in FIG. 7 show a significant decrease in the lag time when 5 mol % of the negatively charged 1-O-DPPE-PEG$_{350}$ is incorporated into the 1-O-DPPC liposomes.

Example 7

Preparation of Micelles Composed of 1-O-DPPE-PEG350, DSPE-PEG750/DPPE-PEG750.

Micelles were made from 1-O-hexadecyl-2-hexadecanoyl-sn-glycero-3-phosphoethanol-amine-N-[methoxy (polyethylene glycol)-350](1-O-DPPE-PEG350), di-octadecanoyl-sn-glycero-3-phosphoethanolamine-N-[methoxy (polyethylene glycol)-750 (DSPE-PEG750). Briefly, weighed amounts of the polymer lipid were dissolved in chloroform. The solvent was removed by a gentle stream of N$_2$. The lipid films were then dried overnight under low pressure to remove trace amounts of solvent. Micelles were made by dispersing the dried polymer lipids in a buffer solution containing: 150 mM KCL, 10 mM HEPES (pH=7.5), 1 mM NaN$_3$, 30 µM CaCl$_2$ and 10 µM EDTA.

Example 8

Permeability Increase of a Target Model Membranes Controlled by Phospholipase $A_2$ Hydrolysis of Micelles Multilamellar model membrane target liposomes were made in the presence of fluorescent calcein in a self-quenching concentration of 20 mM by hydrating a film of 1,2-O-dioctadecyl-sn-glycero-3-phosphatidylcholines (D-O-SPC) in a HEPES buffer solution at pH=7.5 for one hour at 10° C. above the phase transition temperature ($T_m$=55° C.). Unilamellar liposomes were made by extruding the multilamellar liposomes ten times through two stacked 100 nm polycarbonate filters. The unilamellar liposomes were rapidly cooled to a temperature below the transition temperature, and the calcein-containing liposomes were separated from free calcein using a chromatographic column packed with Sephadex G-50. Micelles composed of 1-O-hexadecyl-2-hexadecanoyl-sn-glycero-3-phosphoethanolamine-N-[methoxy(polyethylene glycol)-350](1-O-DPPE-PEG350), di-octadecanoyl-sn-glycero-3-phosphoethanolamine-N-[methoxy(polyethylene glycol)-750 (DSPE-PEG750) were prepared as described in example 7. Calcein release from the target liposome is determined by measuring the fluorescent intensity at 520 nm after excitation at 492 nm.

Figure 8:
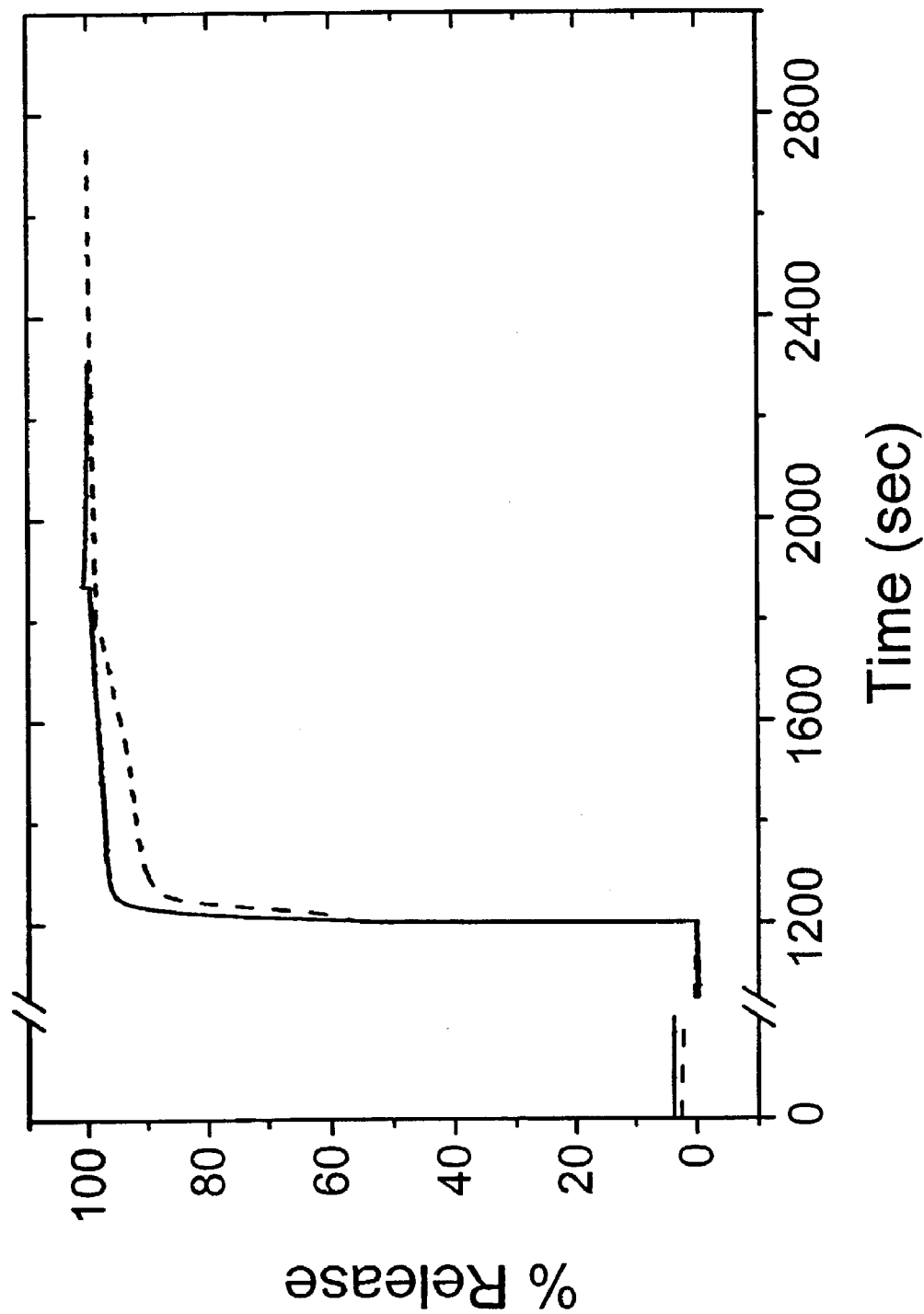
FIG. 8. PLA$_2$-controlled release of the fluorescent model drug calcein across the target membrane of non-hydrolysable D-O-SPC membranes as a function of time for micelles composed of 25 μM 1-O-DPPE-PEG350 (dotted line), DSPE-PEG750 (dashed line) suspended in a 10 mM HEPES-buffer (pH=7.5). Phospholipase A$_2$ (25 nM) was added at time 1200 sec and the temperature was 41° C. The percentage of calcein released is determined as described in FIG. 4. PLA$_2$ catalysed hydrolysis of 1-O-DPPE-PEG350 induced the fastest and highest release.

The concentrations of D-O-SPC and polymer lipid micelles were 25 µM. Snake venom $PLA_2$ (Agkistrodon piscivorus piscivorus) was added (25 nM) to initiate the hydrolytic reaction leading to instant formation of the lyso-lipid and fatty acid hydrolysis products. As calcein is released from the D-O-SPC liposomes, due to the incorporation of the non-bilayer forming polymer-lyso-1-O-lipid and fatty acid into the target lipid membrane, a linear increase in the fluorescence at 520 nm after excitation at 492 nm is observed when calcein is diluted into the surrounding buffer medium as shown in FIG. 8. The percentage of calcein released is determined as described in example 3. $PLA_2$ catalysed hydrolysis of 1-O-DPPE-PEG350 induced the fastest release rate.

Example 9

Hydrolysis of Micelles Composed of DSPE-PEG750

Figure 9:
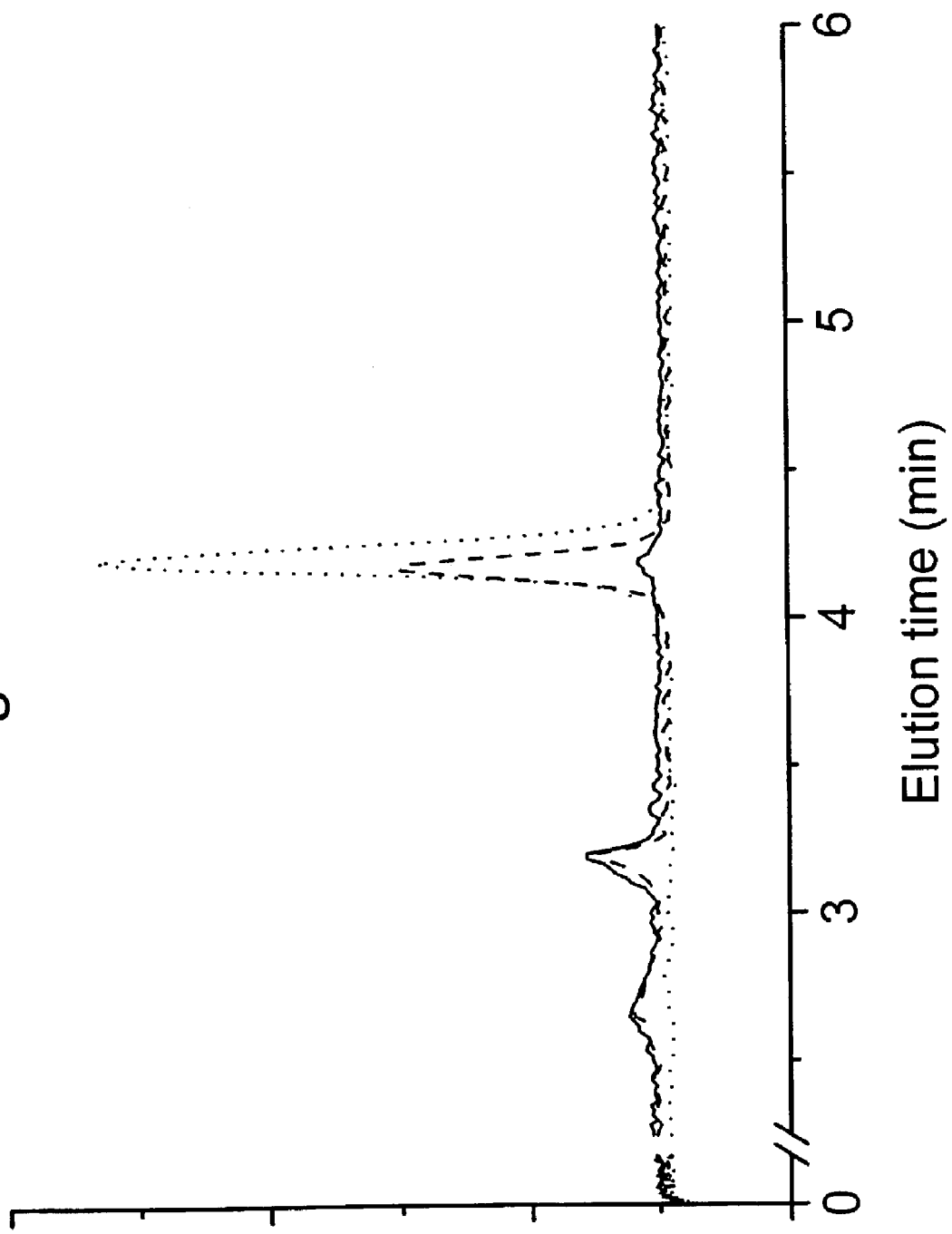
FIG. 9. HPLC chromatograms illustrating the effect of phospholipase A$_2$ hydrolysis of micelles composed DSPE-PEG750 (0.150 mM). The chromatograms show the amount of stearic acid generated before (solid line) phospholipase A$_2$ (A. piscivorus piscivorus) was added to the micelle suspension and the amount (dashed line) of DSPE-PEG750 after the lag-burst. The dotted line show pure stearic acid (0.4 mM). The percentage hydrolysis was calculated on basis of the integrated area of the stearic acid standard (115850 units) and the integrated area of the sample (45630 units). The concentration of the stearic acid in the sample was calculated to (45630/115850×0.4 mM) 0.157 mM, which means that 100% of the DSPE-PEG750 was hydrolysed to lyso-SPE-PEG750 and stearic acid.

The hydrolysis of micelles composed DSPE-PEG750 was followed by analysis of the amount of stearic acid generated. The catalytic reaction was initiated by adding 8.9 µL of a 42 µM $PLA_2$ (150 nM) stock solution to 2.5 ml a thermostated lipid suspension of DSPE-PEG750 (0.150 mM) equilibrated at 45° C. for 600 seconds prior to addition of $PLA_2$. The characteristic burst behavior of $PLA_2$ towards the micelles is signaled by a sudden increase in the intrinsic fluorescence from $PLA_2$ at 340 nm after excitation at 285 nm followed by a concomitant decrease in the 90° light scattering from the lipid suspension (Hønger et al., *Biochemistry* 35, 9003–9006). Samples for HPLC analysis of the amount of stearic acid generated were taken before adding $PLA_2$ and 100 sec after the observed lag-time. The HPLC chromatograms in FIG. 9 shows the amount of stearic acid generated 100 sec after the observed lag time (10 sec) at 45° C. The amount (0.156 mM) of stearic acid generated by hydrolysis was equal to 100% hydrolysis of the DSPE-PEG750 polymer-lipids. HPLC analysis was made using a 5 µm diol column, a mobile phase composed of chloroform/methanol/water (730:230:30, v/v) and an evaporative light scattering detector (see example 2).

Example 10

Model Examples

Liposomes composed of neutral and/or negatively charged phospholipids can act as versatile drug or label delivery systems targeting parasitic diseases in tissues with elevated levels of $PLA_2$ due to the parasitic infection, organs of special interest are the liver, spleen and bone marrow. When administered intravenously these liposomes have a strong tendency to accumulate in the liver and spleen due to a combination of physicochemical factors relating to the lipid composition of the liposomes and physiological factors involving the rich blood supply and abundance of macrophages in the liver and spleen. In the examples herein are described an experimental model system illustrating a new principle for improved drug or label delivery which takes advantage of an elevated activity of extracellular phospholipase $A_2$ in the infected liver or spleen tissue. The phospholipase $A_2$ hydrolyses a lipid-based proenhancer in the carrier liposome, producing lyso-phospholipid and free fatty acid, which are shown in a synergistic way to lead to enhanced liposome destabilisation and drug release at the same time as the permeability of the target membrane is enhanced. The proposed system can be made thermosensitive and offers a rational way for developing smart liposome-based delivery systems by incorporating into the carrier specific lipid-based proenhancers, prodestabilisers or prodrugs that automatically become activated by phospholipase $A_2$ only at the diseased and infected target sites.

Figure 10:
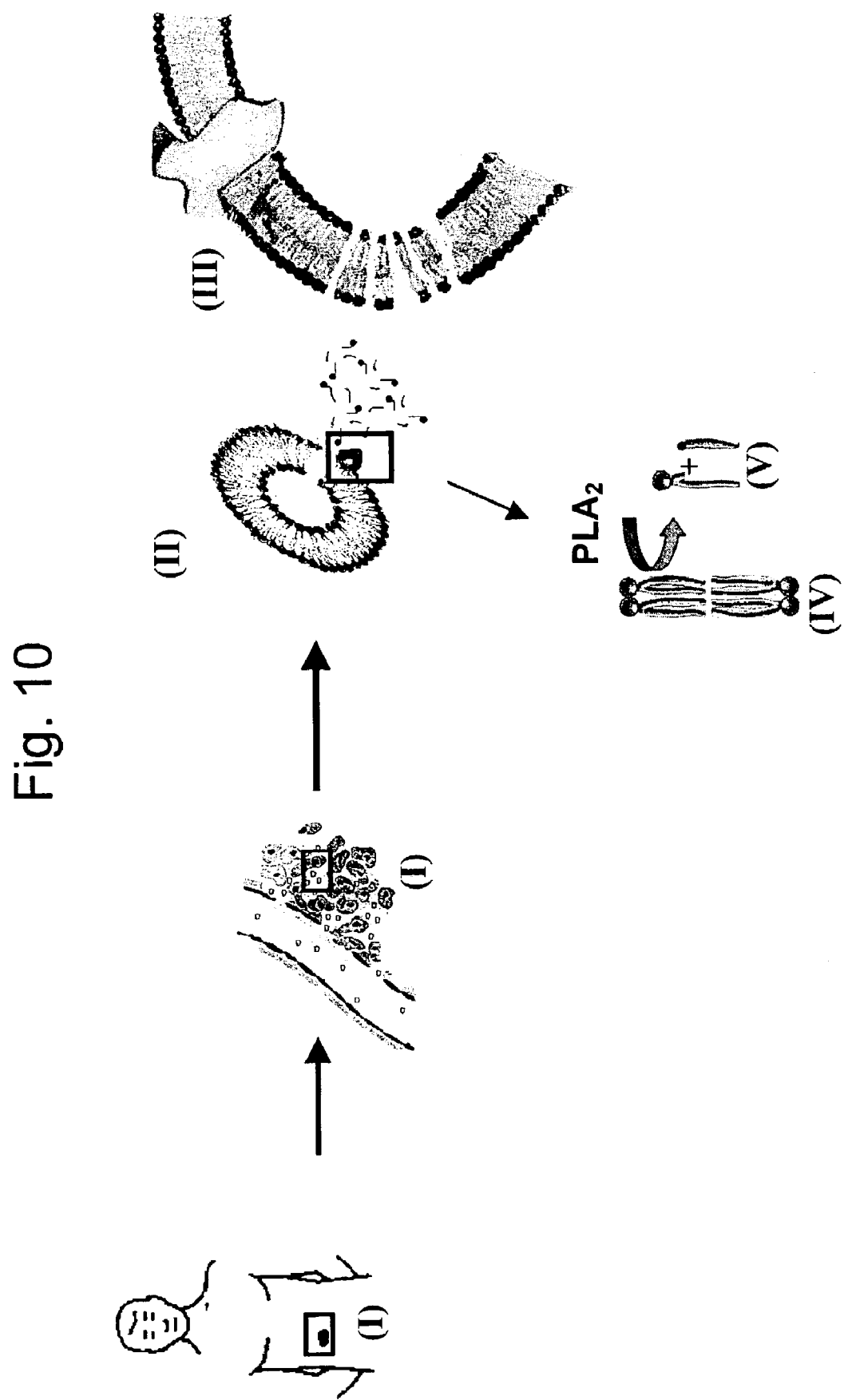
FIG. 10. Describes the principle of liposomal drug targeting, release and absorption by extracellular enzymes.
(I) Reticuloendothelial system, e.g. macrophages in liver and spleen infected with parasites (i.e. Leishmania)
(II) Prodrug carrier liposome
(III) Target parasitic cell and cell membrane
(IV) Prodrug (i.e. monoether-lipid), proenhancer (lipid), proactivator (lipid)
(V) Drugs (i.e. ether-lysolipid and fatty acid derivatives) enhancers (lysolipid+fatty acid) PLA$_2$ activators (lysolipid+fatty acid)

Liposomes are self-assembled lipid systems and their stability is therefore to a large extent controlled by non-specific physical interactions. Insight into the molecular control of the physical properties of liposomes is therefore important for manipulating and tailoring the liposomal properties in relation to specific drug-delivery purposes. As an example, the thermally induced gel-fluid lipid phase transition has been exploited and optimised design systems for enhanced release of drugs due to hyperthermia. It would be desirable if an intelligent and versatile drug-delivery system could be designed which has built in a dual virtual trigger mechanism of simultaneous (i) enhanced drug release selectively in the infected target tissue and (ii) enhanced transport of the drug or label into the infected cells. This principle is illustrated schematically in FIG. 10.

By the examples herein is described the development of a simple and operative experimental biophysical model system which sustains such a dual mechanism to be triggered at the infected target sites such as liver and spleen. The model assumes elevated activity of extracellular phospholipase $A_2$ in the infected tissue as is the case in inflamed and cancerous tissue where the level of extracellular $PLA_2$ can be manifold magnified. Upon exposure to extracellular $PLA_2$, the phospholipids of negatively charged liposomes have been shown to suffer enhanced hydrolysis compared to neutral liposomes. This leads to destabilisation of the liposome and enhanced release of the encapsulated drug or label. The hydrolysis products, lyso-phospholipids and free fatty acids, act in turn as absorption enhancers for drug or label permeation across the target membrane. In this way the phospholipids of the carrier liposome behave as prodestabilisers at the site of the carrier and as proenhancers at the site of the target membrane. Molecular details of this principle are illustrated schematically in FIG. 11.

The experimental model system consists of a negatively charged liposome carrier and a model target membrane. The carrier is a 100 nm unilamellar liposome made of dipalmitoyl phosphatidylcholine lipids (DPPC) with a small amount (2.5 mol %) of negatively charged lipid of the type dipaimitoyl phosphatidylethanolamine (DPPE)-$PEG_{2000}$. The target membrane is another liposome made of 1,2-O-dioctadecyl-sn-glycero-phosphatidylcholine (D-O-SPC) which is a phospholipid where the acyl linkages of the stearoyl chains are ether bonds. In contrast to DPPC, D-O-SPC is inert towards $PLA_2$-catalysed hydrolysis thereby mimicking the stability of an intact target cell membrane toward degradation by its own enzymes. This experimental assay, which permits simultaneous as well as separate investigation of the effect of destabilisers at the carrier liposomes and the effect of enhancers at the target membrane, involves entrapment of a water-soluble fluorescent calcein model drug in a self-quenching concentration, in the interior of the non-hydrolysable target liposome, rather than in the carrier liposome. The enhanced level of extracellular $PLA_2$ at the target membrane can then be simulated by adding extracellular $PLA_2$ to initiate the hydrolytic reaction in a suspension of the carrier and target liposomes. The permeation of calcein across the D-O-SPC target membrane is subsequently monitored by the increase in fluorescence. In order to investigate the effect of the presence of small amounts of negatively charged PEG-lipids in the carrier liposome, a similar experiment was performed with conventional bare DPPC liposomes. Furthermore, in order to compare and discriminate the permeability enhancing effect of lyso-phospholipids from that of free fatty acids, experiments without enzymes were carried out where lyso-phospholipids and free fatty acids were added simultaneously or separately to the target liposomes.

Figure 12A:
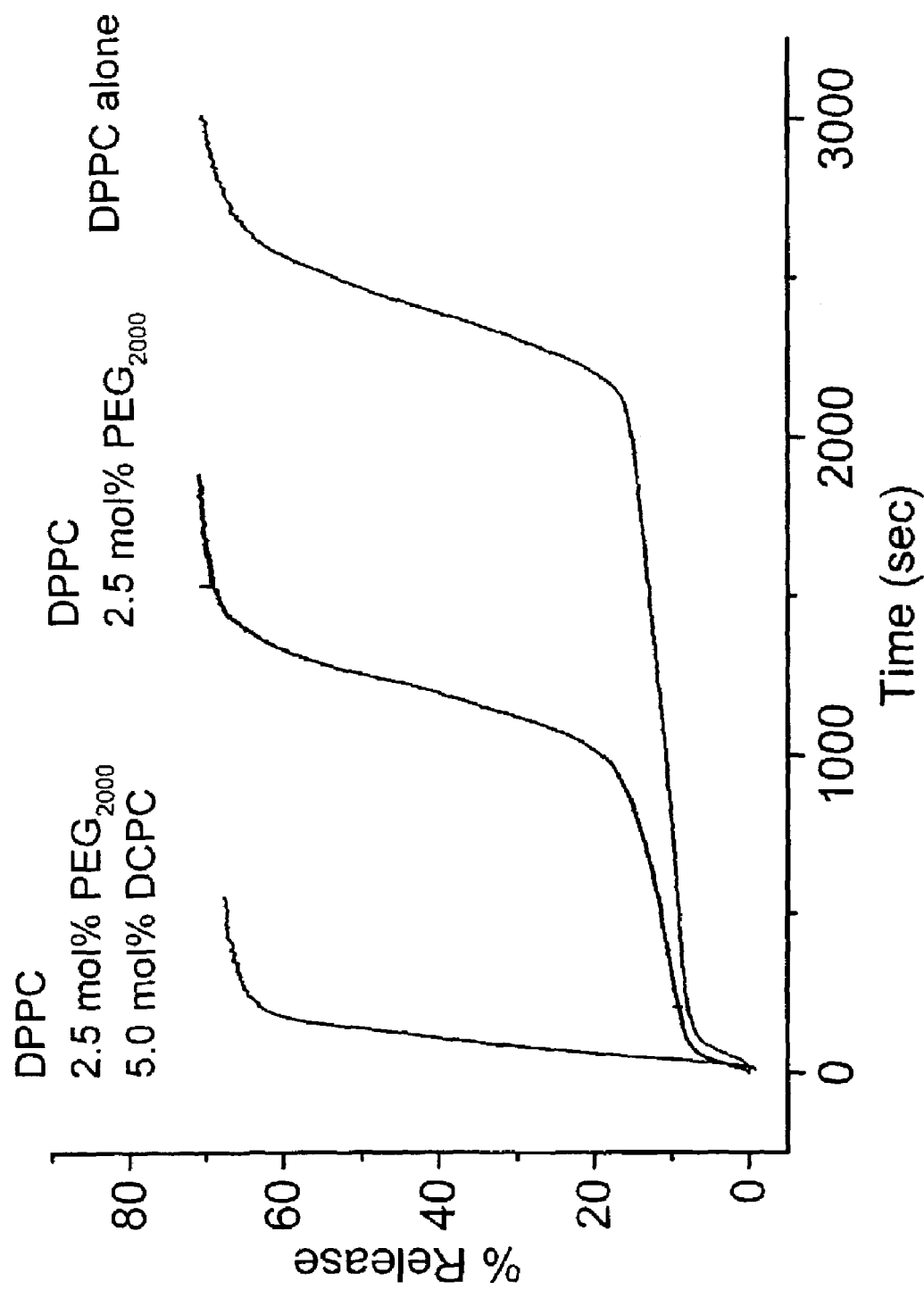
FIG. 12(a) PLA$_2$-controlled release of the fluorescent model drug calcein across the target membrane as a function of time for different compositions of the carrier liposomes. The temperature is 37° C. In comparison with bare DPPC carriers, the rate of release of the model drug is dramatically enhanced for the carriers incorporated with 2.5 mol % of the negatively charged DPPE-PEG2000. A further augmentation of the rate of release is obtained if the carrier also contains a short-chain phospholipid, didecanoylphosphatidylcholine (DCPC), which acts as a local activator for the enzyme. The percentage of calcein released is determined as % Release=100 $(I_{F(t)}-I_B)/(I_T-I_B)$, where $I_{F(t)}$ is the measured fluorescence at time t after addition of the enzyme, $I_B$ is the background fluorescence, and $I_T$ is the total fluorescence measured after addition of Triton X-100 which leads to complete release of calcein by breaking up the target liposomes. (b) PLA$_2$-controlled release of the fluorescent model drug calcein across the target membrane as a function of time for different temperatures. As the temperature is raised, the rate of release is enhanced due to increased activity of the enzyme induced by structural changes in the lipid bilayer substrate of the carrier liposome. In the present assay a maximum release of about 70% is achieved in all cases. The insert shows the time of 50% calcein release, $t_{50\%}$, as a function of temperature. The concentration of the target and carrier liposomes are 25 μM, and PLA$_2$ is added in a 25 nM concentration in a HEPES buffer with pH=7.5.
Figure 12B:
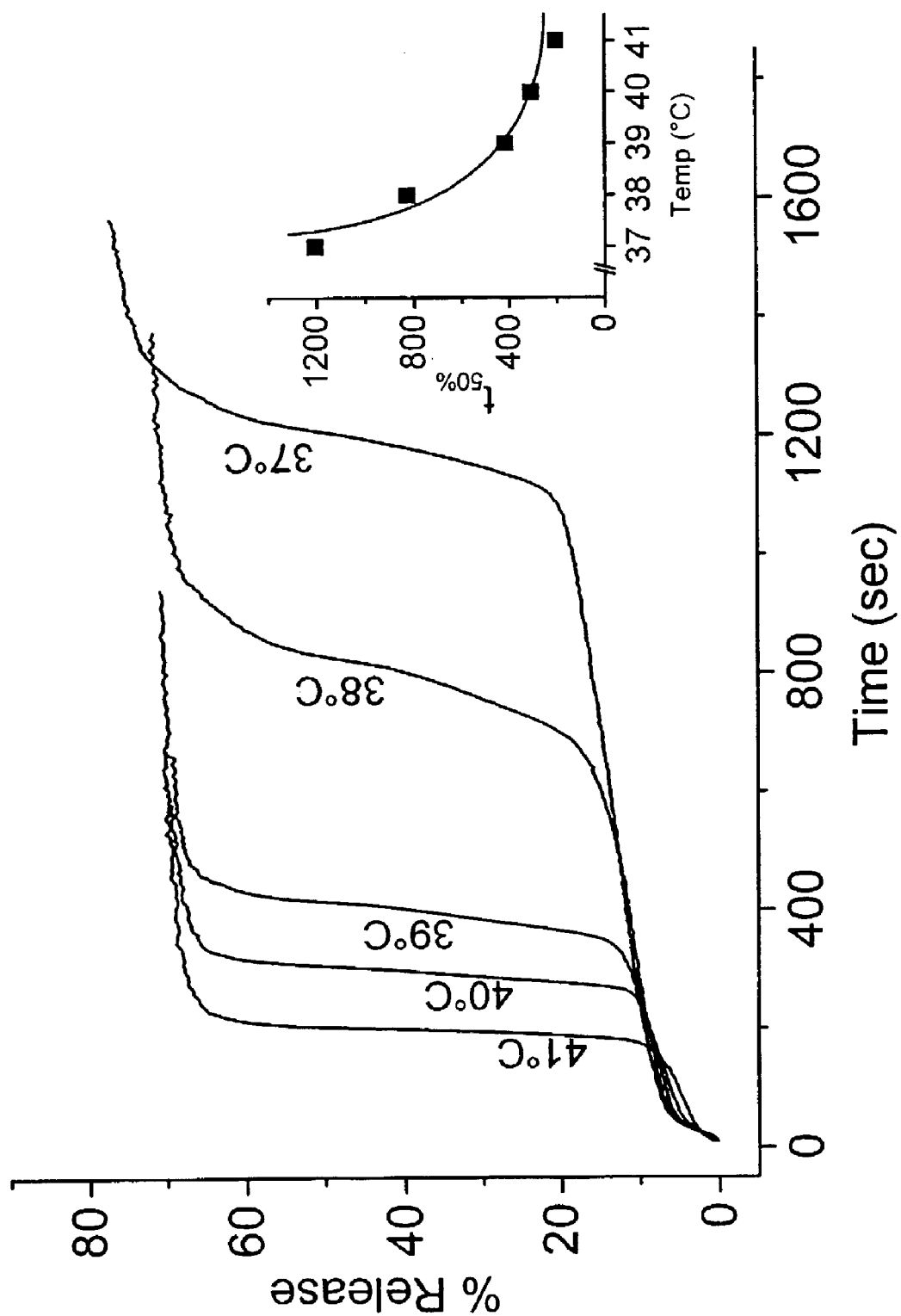

In FIG. 12.a are shown the results for the release of calcein as a function of time after adding $PLA_2$ to the system. The reaction time-course of the particular $PLA_2$ used has a characteristic lag-burst behavior with a so-called lag time which conveniently can be used as a measure of the enzymatic activity. A dramatic decrease in the lag time and a concomitant enhancement of the rate of release are observed when the carrier liposomes contain the negatively charged, $DPPE-PEG_{2000}$, in accordance with previous findings of enhanced extracellular $PLA_2$ degradation of negatively charged polymer-coated liposomes.

Figure 13:
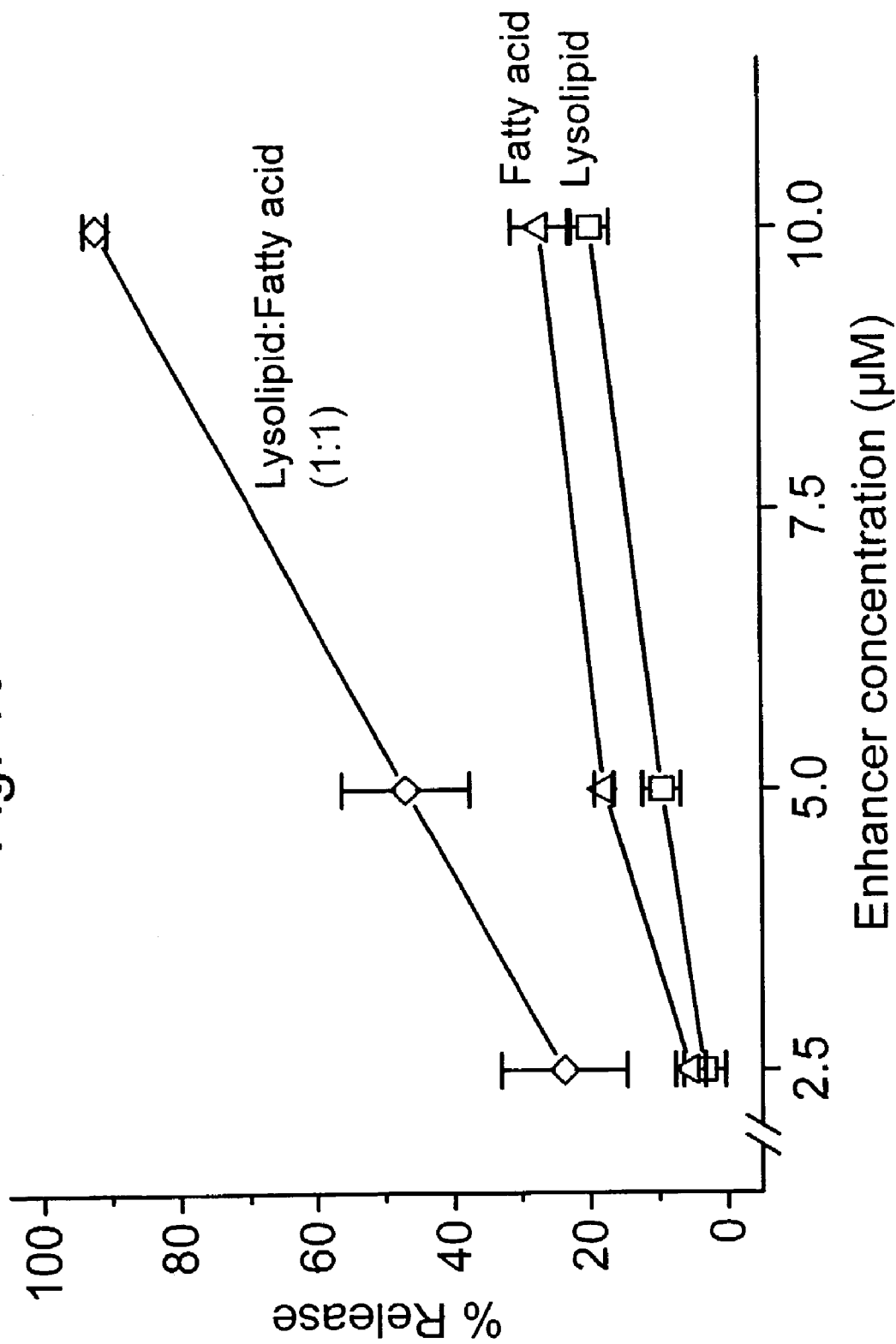
FIG. 13. Total release after 20 min of the fluorescent model drug calcein across the target membrane as a function of adding increasing amounts of lyso-palmitoyl phospholipid and palmitic acid, separately, and in a 1:1 mixture. The concentration of the target membranes is 25 µM in a HEPES buffer with pH=7.5 at a temperature of 39° C.

These results suggest that the products of the $PLA_2$-catalysed hydrolysis of the DPPC lipids of the DPPC-liposomal carrier, lyso-phospholipid and free fatty acid, which are produced in a 1:1 mixture, are incorporated into the target membrane, leading to a large increase in membrane permeability. These products, which have very low water solubility, are known, due to their non-cylindrical molecular shapes, to induce a curvature stress field in the membrane or small-scale lateral phase separation which induce membrane defects and increased permeability. This is substantiated by the data in FIG. 13 which show that the addition of lyso-phospholipid or fatty acid separately to the present target system, in the absence of $PLA_2$, leads to an increased rate of calcein release across the target membrane. However, the crucial finding is that if lyso-phospholipid and free fatty acid are added simultaneously in a 1:1 mixture, a dramatic enhancement in the rate of release is observed as shown in FIG. 13. This strongly suggests that the two enhancers act in a synergistic fashion, thereby highlighting the unique possibility in exploiting $PLA_2$-catalysed hydrolysis for combined destabilisation of the carrier liposome and enhancement of drug transport across the target membrane. The synergistic effect is further augmented by the fact that extracellular $PLA_2$ is activated by its own hydrolysis products revealing the degradable phospholipids of the carrier liposome as a kind of proactivators.

It should be pointed out that the effect in the present drug-delivery model system of using lipids as proenhancers and prodestabilisers via extracellular $PLA_2$ activity is dynamic and refers to an intrinsic time scale. This time scale is the effective retention time of the carrier liposomes near the target membrane. The more rapidly the enzyme becomes active, the faster is the drug release and the larger the drug absorption during the time which the carrier spends near the target. Furthermore, the faster the enzyme works the more readily it becomes available for hydrolysis of other drug-carrying liposomes that approach the diseased target site. Once it has been established that extracellular $PLA_2$ activity can be used to control drug release, several rational ways open up for intelligent improvements of the proposed drug-delivery system via use of well-known mechanisms of altering extracellular $PLA_2$ activity by manipulating the physical properties of the lipid bilayer to which the enzyme is known to be sensitive. Hence the strategy is to modify certain physical properties of the carrier liposomes without significantly changing their vascular circulation time. We shall illustrate this general principle by demonstrating the effects of both a physico-chemical factor, the lipid composition of the carrier, and an enviromental (thermodynamic) factor, the local temperature at the target site.

Short-chain phospholipids, such as didecanoyl phosphatidylcholine (DCPC), activate extracellular $PLA_2$. The effect on calcein permeation across the target membranes induced by incorporation of a small amount of DCPC into the carrier PEG-liposomes is also shown in FIG. 12.*a*. The release is very fast due to an almost instantaneous activation of the enzyme. We have furthermore found that extracellular $PLA_2$ becomes deactivated (data not shown) when a large amount of cholesterol (≈20 mol %) is incorporated into liposomes. In contrast we find that a small amount of cholesterol (≈3 mol %) activates extracellular $PLA_2$.

Temperature is known to have a dramatic and highly non-linear effect on extracellular $PLA_2$ activation in the region of the gel-fluid phase transition of saturated phospholipid bilayers. This effect is not caused by changes in the enzyme but by dramatic lateral structural changes in the lipid bilayer. It is possible to take advantage of this effect in the present drug-delivery system as suggested by the data in FIG. 12.*b*. As the temperature approaches the transition temperature at 41° C., the rate of calcein release is progressively enhanced as quantified by the time of 50% calcein release, $t_{50\%}$, shown in the insert to FIG. 12.*b*. It has previously been suggested that hypertermia could be exploited to enhance drug release, and that local heating at predefined infected areas could be used to locally destabilise drug-carrying liposomes, by exploiting the enhanced leakiness of liposomes at their phase transition. In the new model drug-delivery system proposed here, these thermosensitive possibilities are integrated and fully exploited via the thermal sensitivity of extracellular $PLA_2$ to the physical properties of the carrier liposome. In contrast to the case where the thermic effect can only be achieved by a local temperature increase using external heating sources at a predetermined infected site of some minimal size, the $PLA_2$-controlled release will be enhanced everywhere where temperature and extracellular $PLA_2$ concentration are elevated, e.g. in infected tissue, independent of the size of the diseased region and without requiring a preceding localisation of the diseased tissue.

DPPC, DCPC, D-O-SPC, and DPPE-$PEG_{2000}$ were obtained from Avanti Polar Lipids. Purified snake venom $PLA_2$ (Agkistrodon piscivorus piscivorus) was a generous gift from dr. R. L. Biltonen. This $PLA_2$ enzyme belongs to the class of low-molecular weight, 14 kD secretory enzymes which display structural similarity to human extracellular phospholipase $A_2$. Multilamellar target liposomes in the presence of fluorescent calcein in a self-quenching concentration of 20 mM were made by hydrating a film of D-O-SPC in a HEPES buffer solution at pH=7.5 for one hour at 10° C. above the phase transition temperature $T_m$=55° C. Unilamellar liposomes were made by extruding the multilamellar liposomes ten times through two stacked 100 nm polycarbonate filters. The unilamellar liposomes were rapidly cooled to a temperature below the transition temperature, and the calcein-containing liposomes were separated from free calcein using a chromatographic column packed with Sephadex G-50. The unilamellar carrier liposomes of DPPC, DCPC and DPPE-PEG$_{2000}$ were prepared in a similar fashion T$_m$=41° C.). Calcein release from the target liposomes is determined by measuring the fluorescent intensity at 520 nm after excitation at 492 nm. All measurements are performed at temperatures where the lipids of both the carrier and target liposomes are in the gel state.

Example 11

Phospholipase A$_2$ Concentration Dependent Release Assay

Multilamellar 1-O-DPPC-liposomes with 10 mol % 1-O-DPPE-PEG350 were made in the presence of fluorescent calcein in a self-quenching concentration of 20 mM by hydrating a film of 90% 1-O-hexadecyl-2-hexadecanoyl-sn-glycero-3-phosphocholine and 10% 1-O-hexadecyl-2-hexadecanoyl-sn-glycero-3-phosphoethanolamine-N-[methoxy (polyethylene glycol)-350] in a HEPES buffer solution at pH=7.5 for one hour at 10° C. above the phase transition temperature. Unilamellar liposomes were formed by extruding the multilamellar liposomes ten times through two stacked 100 nm polycarbonate filters. The unilamellar liposomes were rapidly cooled to a temperature below the transition temperature, and the calcein-containing liposomes were separated from free calcein using a chromatographic column packed with Sephadex G-50.

Figure 14:
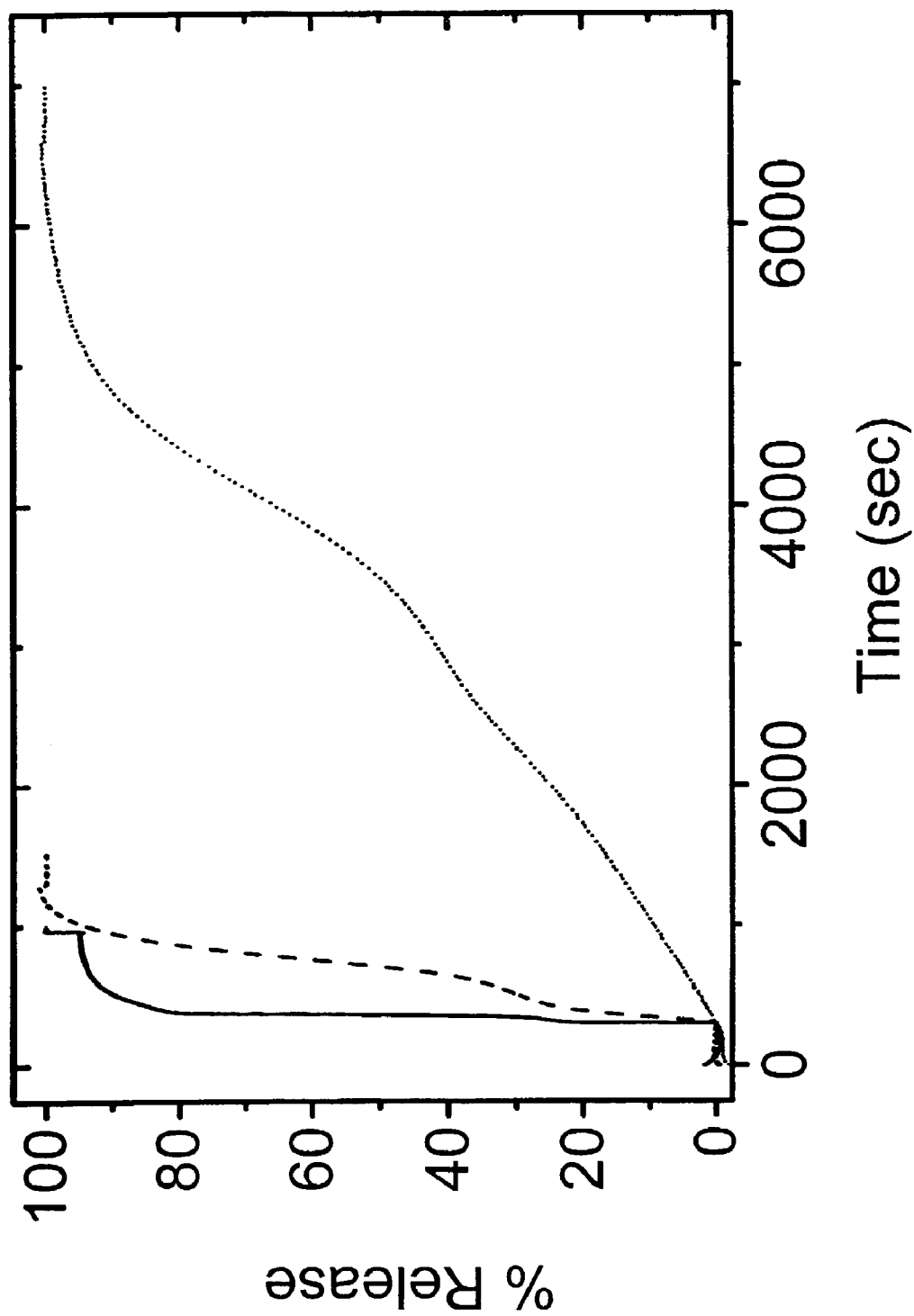
FIG. 14 $PLA_2$-controlled release of the fluorescent model drug calcein from liposomes composed of 25 µM 90 mol % 1-O-DPPC and 10 mol % of the negatively charged 1-O-DPPE-PEG350 suspended in a 10 mM HEPES-buffer (pH=7.5), as a function of time. 50 nM (straight line), 1 nM (solid line) and 0.02 nM (dotted line) phospholipase $A_2$ (A. piscivorus piscivorus) was added at time 300 sec, the temperature was 35.5° C. The percentage of calcein released is determined as describe in FIG. 4.

Assay conditions for the PLA$_2$ induced calcein release were 25 µM unilamellar liposomes, 50, 1 and 0.02 nM PLA$_2$, 150 mM KCL, 10 mM HEPES (pH 7.5), 1 mM NaN$_3$, 30 µM CaCl$_2$, and 10 µM EDTA. PLA$_2$ was added to 2.5 ml of the thermostated micelle suspension equilibrated for at least 300 sec at 35.5° C. prior to addition of PLA$_2$. The percentage of calcein released is determined as: % Release=100×($I_{F(t)}$-$I_B$)/($I_T$-$I_B$), where $I_{F(t)}$ is the measured fluorescence at time t after addition of the enzyme, $I_B$ is the background fluorescence, and $I_T$ is the total fluorescence measured after addition of Triton X-100 which leads to complete release of calcein by breaking up the 1-O-DPPC-liposomes. FIG. 14 show that the induced release of calcein was slowest when only 0.02 nM PLA$_2$ was added to the liposome suspension.

Example 12

Hydrolysis of Negatively Charged Liposomes by Phospholipase A2 in Cell-Free Rat Peritoneal Fluid Cell-free peritoneal fluid from rat with casein-induced acute inflammation was prepared by injecting 5 ml 1% sodium caseinate into the peritoneal cavity of a SRPD male rat, weighing 250–260 g. The rat was sacrificed by bleeding after 24 hours and the inflammatory fluid was collected from the peritoneum and centrifuged at 1500 G for 20 min in order to obtain a cell-free peritoneal fluid.

Negatively charged fully hydrated unilamellar liposomes with a narrow size distribution were prepared from 89 mol % di-hexadecanoyl-sn-glycero-3-phosphoglycerol (DPPG), 10 mol % 1-O-hexadecyl-2-hexadecanoyl-sn-glycero-3-phosphoethanolamine-N-[methoxy(polyethylene glycol)-350] (1-O-DPPE-PEG350) and 1 mol % 1,2-bis-(1-pyrene-decanoyl)-sn-glycero-3-phosphocholine (bis-py-DPC). Bis-py-DPC is a PLA2 substrate with two adjacent pyrene fluorophores that form excited-state dimers (eximers) emitting at 470 nm upon excitation at 342 nm. Phospholipase catalysed hydrolysis separates the two fluorophores, which then emit at 380 nm (monomers).

Figure 15:
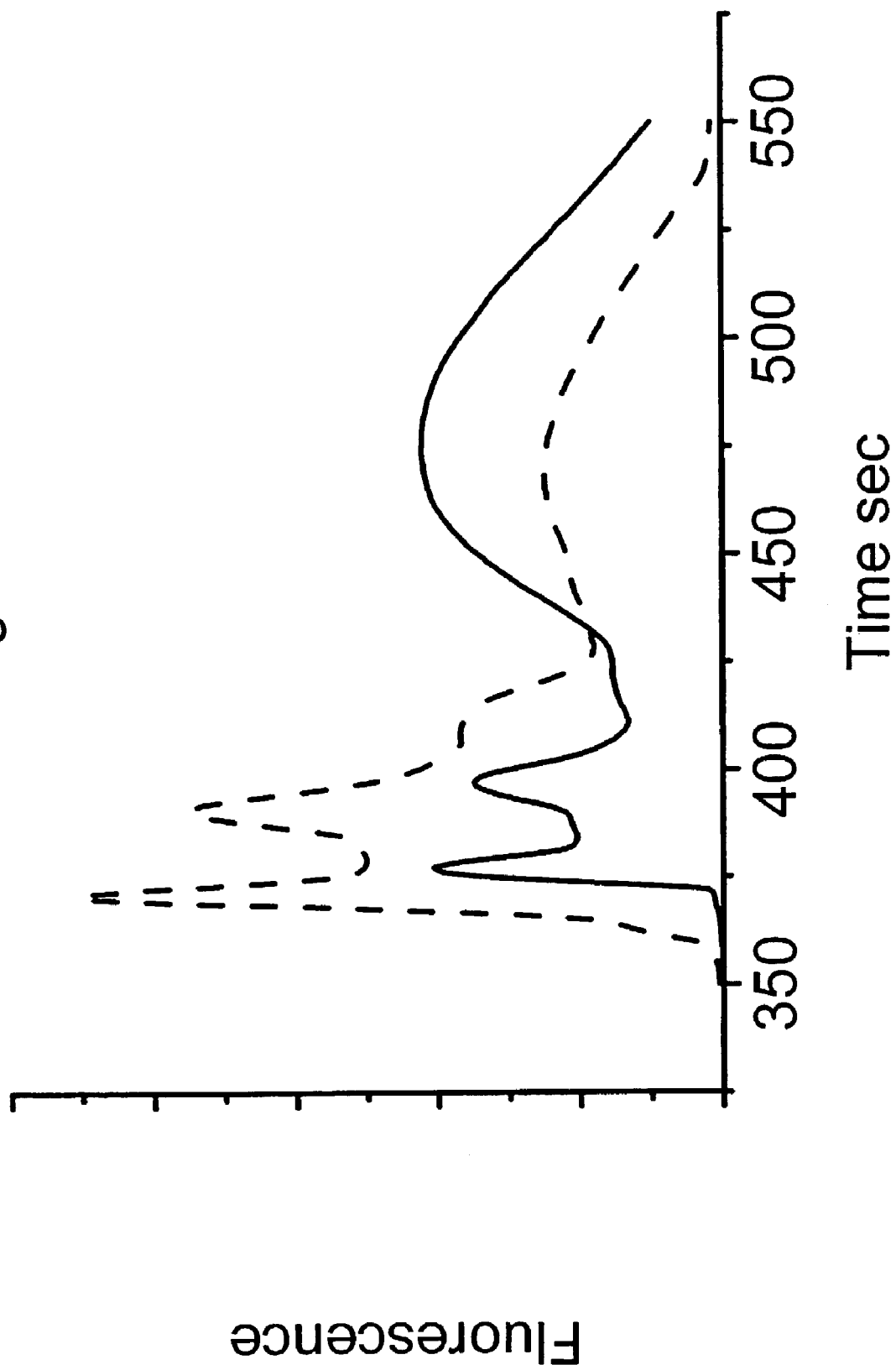
FIG. 15. Emission spectrum of 1 mol % bis-py-DPC incorporated in negatively charged liposomes (0.100 mM) before (solid line) and after (dashed line) adding 100 nM $PLA_2$ (Agkistrodon piscivorus piscivorus) to a liposome suspension equilibrated at 41° C.

FIG. 15 shows the emission spectra obtained after excitation at 342 nm of bis-py-DPC incorporated in negatively charged liposomes (0.100 mM) before and after adding 100 nM PLA$_2$ (Agkistrodon piscivorus piscivorus). The observed changed in the emissions spectrum after phospholipase mediated hydrolysis is used in a continuos assay, measuring the eximer emission at 470 nm simultaneously with the monomer emission at 380, upon excitation at 342 nm. FIG. 16 shows the reaction time profile of rat phospholipase A$_2$ catalysed hydrolysis of the negatively charged liposomes. The catalytic reaction was initiated by adding cell-free peritoneal fluid to 2.5 ml of a thermostated liposome suspension equilibrated for 60 sec prior to addition of PLA$_2$. The characteristic lag-burst behavior of the phospholipase is signaled by a sudden increase in the monomer fluorescence at 380 nm and a subsequent decrease in the eximer fluorescence as shown at the insert on FIG. 16.

Assay conditions for the PLA$_2$ reaction time profile shown in FIG. 16 were: 0.100 mM unilamellar negatively charged liposomes, 100 µl undiluted cell-free peritoneal fluid, 10 mM HEPES (pH 7.5), 5 mM CaCl$_2$, and 150 mM NaCl.

The invention claimed is:

1. A method for the systemic treatment of parasitic infections of a mammal in need of treatment thereof, said parasitic infection being characterized by increasing the PLA$_2$ level in said mammal by administering to the mammal an efficient amount of a lipid-based drug delivery system comprising (A) a first active drug substance selected from lysolipid derivatives, wherein the active drug substance is present in the lipid-based system in the form of a prodrug, said prodrug being a lipid derivative having (a) an aliphatic group of a length of at least 7 carbon atoms and an organic radical having at least 7 carbon atoms, and (b) a hydrophilic moiety, said prodrug furthermore being a substrate for extracellular phospholipase A2 to the extent that the organic radical can be hydrolytically cleaved off, whereas the aliphatic group remains substantially unaffected, whereby the first active drug substance is liberated in the form of a lysolipid derivative which is not a substrate for lysophospholipase, and (B) a second drug substance which is a therapeutically and/or prophylactically active substance selected from the group consisting (i) anti-parasitic agents, (ii) antibiotics and anti-fungals, and (iii) anti-inflammatory agents, wherein the lipid-based drug delivery system is in the form of liposomes.

2. A method according to claim 1, wherein the increased level of PLA$_2$ is localized to a specific tissue and/or organ of the mammal, said tissue and/or organ being infected by the parasite.

3. A method according to claim 1, wherein the parasitic infection involves the liver and/or the spleen of the mammal.

4. A method according to claim 1, wherein the organic radical which can be hydrolytically cleaved off, is an auxiliary drug substance or an efficiency modifier for the active drug substance.

5. A method according to claim 1, wherein the prodrug is a lipid derivative of the following formula:

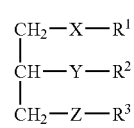

wherein
- X and Z independently are selected from O, $CH_2$, NH, NMe, S, S(O), and $S(O)_2$;
- Y is —OC(O)—, Y then being connected to $R^2$ via either the oxygen or carbonyl carbon atom;
- $R^1$ is an aliphatic group of the formula $Y^1Y^2$;
- $R^2$ is an organic radical having at least 7 carbon atoms;
- where $Y^1$ is $-(CH_2)_{n1}-(CH=CH)_{n2}-(CH_2)_{n3}-(CH=CH)_{n4}-(CH_2)_{n5}-(CH=CH)_{n6}-(CH_2)_{n7}-(CH=CH)_{n8}-(CH_2)_{n9}$, and the sum of $n1+2n2+n3+2n4+n5+2n6+n7+2n8+n9$ is an integer of from 9 to 29; n1 is zero or an integer of from 1 to 29, n3 is zero or an integer of from 1 to 20, n5 is zero or an integer of from 1 to 17, n7 is zero or an integer of from 1 to 14, and n9 is zero or an integer of from 1 to 11; and each of n2, n4, n6 and n8 is independently zero or 1; and $Y^2$ is $CH_3$ or $CO_2H$; where each $Y^1-Y^2$ independently may be substituted with halogen or $C_{1-4}$-alkyl,
- $R^3$ is selected from phosphatidic acid ($PO_2$—OH), derivatives of phosphatidic acid and bioisosters to phosphatic acid and derivatives thereof.

6. A method according to claim 5, wherein $R^2$ is an aliphatic group of a length of at least 7 carbon atoms.

7. A method according to claim 1, wherein $R^2$ is a group of the formula $Y^1Y^2$.

8. A method according to claim 1, wherein at least a fraction of the prodrug is of the formula defined in claim 5, wherein $R^3$ is a derivative of phosphatidic acid to which a polymer selected from polyethylene glycol, poly(lactic acid), poly(glycolic acid), poly(lactic acid)-poly(glycolic acid) copolymers, polyvinyl alcohol, polyvinylpyrrolidone, polymethoxa-zoline, polyethyloxazoline, polyhydroxypropyl methacrylamide, polymethacrylamide, polydimethylacrylamide, and derivatised celluloses, is covalently attached.

9. A method according to claim 1, wherein the prodrug constitutes 15–100 mol % of the total dehydrated lipid-based system.

10. A method according to claim 1, wherein the lipopolymer, if present, constitutes 0.1–10 mol % of the total dehydrated system.

11. A method according to claim 1, wherein the parasitic infection is caused by a parasitic organism selected from the group consisting of *Leishmania, Plasmodium falciparum, Plasmodium vivax, Plasmodium ovale, Entamoeba histolytica* and *Chlornorchis sinensis*.

12. A method according to claim 1 for intravenous administration.

* * * * *